US009308341B2

(12) United States Patent
Neely

(10) Patent No.: US 9,308,341 B2
(45) Date of Patent: Apr. 12, 2016

(54) OXYGEN DELIVERY APPARATUS, SYSTEM, AND METHOD

(76) Inventor: Travis Ray Neely, Murphy, TX (US)

( * ) Notice: Subject to any disclaimer, the term of this patent is extended or adjusted under 35 U.S.C. 154(b) by 601 days.

(21) Appl. No.: 13/356,386

(22) Filed: Jan. 23, 2012

(65) Prior Publication Data
US 2013/0032148 A1 Feb. 7, 2013

Related U.S. Application Data

(63) Continuation-in-part of application No. 13/313,634, filed on Dec. 7, 2011, and a continuation-in-part of application No. 13/313,707, filed on Dec. 7, 2011, and a continuation-in-part of application No. 13/313,559, filed on Dec. 7, 2011.

(60) Provisional application No. 61/515,211, filed on Aug. 4, 2011.

(51) Int. Cl.
*A61M 16/06* (2006.01)
*A61M 16/16* (2006.01)
(Continued)

(52) U.S. Cl.
CPC ........... *A61M 16/06* (2013.01); *A61M 16/0666* (2013.01); *A61M 16/0672* (2014.02);
(Continued)

(58) Field of Classification Search
CPC ........ A62B 7/04; A62B 9/027; A62B 18/084; A62B 18/00; A62B 18/02; A62B 18/08; A62B 7/00; A62B 9/00; A62B 9/02; A61B 5/097; A61B 5/0836; A61B 5/6819; A61B 5/08; B63C 11/24; A61M 16/00; A61M 16/104; A61M 16/20; A61M 16/202; A61M 16/207; A61M 16/0677; A61M 16/10; A61M 16/0666; A61M 16/0858; A61M 16/208; A61M 16/1045; A61M 16/06; A61M 16/0886; A61M 16/0633; A61M 16/0616; A61M 16/201; A61M 16/0694; A61M 16/0057; A61M 11/00; A61M 15/08; A61M 16/0672; A61M 16/0683; A61M 16/085; A61M 16/18; A61M 25/02; B64D 10/00
USPC ............. 128/200.24, 200.26, 203.12, 203.15, 128/203.22, 205.25, 206.11, 207.13, 128/207.18, 200.11, 201.22, 203.25, 128/203.27, 204.18, 204.19, 204.21, 128/204.22, 204.23, 204.24, 204.26, 128/205.12, 205.23, 205.24, 206.21, 128/206.27, 207.11, 207.16
See application file for complete search history.

(56) References Cited

U.S. PATENT DOCUMENTS 2,104,016 A    1/1938   Biggs
2,663,297 A  * 12/1953  Turnberg .................. 128/207.13
(Continued)

FOREIGN PATENT DOCUMENTS

GB           876184     *  8/1961

OTHER PUBLICATIONS

Legend Medical Devices, Inc., Legend M.D. Anesthesia, CPAP, Respiratory Care and Infection Control Products: Manufacturer Direct Supply, http://www.legendmd.com/legend_catalog_2007.pdf, 2007, printed Apr. 2, 2013.
(Continued)

*Primary Examiner* — Annette Dixon
(74) *Attorney, Agent, or Firm* — Hitchcock Evert LLP

(57) ABSTRACT

A system, method, and apparatus for air delivery. A cannula having a low velocity airflow and efficient air delivery system. The cannula includes at least one compartment to reduce airflow velocity and nostril inserts. The cannula may further include moldable components and materials to increase comfort and minimize chafing of a wearer. The cannula further may include a head strap to hold the mask in position on a user's head, where said harness minimizes chafing of the user.

8 Claims, 14 Drawing Sheets

Figure 1:
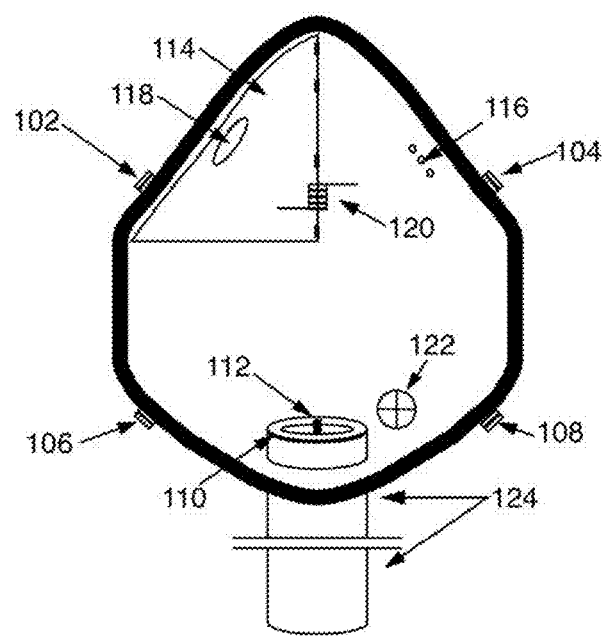

(51) Int. Cl.
   *A61M 16/10* (2006.01)
   *A61M 16/20* (2006.01)
   *A61M 16/00* (2006.01)
   *A61M 11/00* (2006.01)
   *A61M 16/08* (2006.01)

(52) U.S. Cl.
   CPC ....... *A61M16/0677* (2014.02); *A61M 16/0683* (2013.01); *A61M 16/0694* (2014.02); *A61M 11/00* (2013.01); *A61M 16/0078* (2013.01); *A61M 16/0875* (2013.01); *A61M 16/16* (2013.01); *A61M 2016/0015* (2013.01); *A61M 2202/0208* (2013.01); *A61M 2205/11* (2013.01); *A61M 2205/12* (2013.01); *A61M 2205/13* (2013.01); *A61M 2205/18* (2013.01); *A61M 2205/42* (2013.01)

(56) References Cited

U.S. PATENT DOCUMENTS

| | | | |
|---|---|---|---|
| 2,928,387 A | | 3/1960 | Layne |
| 3,700,000 A | * | 10/1972 | Hesse et al. ................... 137/494 |
| 3,726,275 A | * | 4/1973 | Jackson et al. ............ 128/207.18 |
| 3,863,630 A | * | 2/1975 | Cavallo .................... 128/203.27 |
| 4,248,218 A | * | 2/1981 | Fischer .................... 128/204.18 |
| 4,705,033 A | | 11/1987 | Halfpenny |
| 5,301,667 A | | 4/1994 | McGrail et al. |
| 5,357,945 A | | 10/1994 | Messina |
| 5,400,776 A | * | 3/1995 | Bartholomew ......... 128/200.24 |
| RE35,339 E | | 10/1996 | Rapoport |
| 5,586,551 A | | 12/1996 | Hilliard |
| 5,988,162 A | | 11/1999 | Retallick, III |
| 6,240,921 B1 | | 6/2001 | Brydon et al. |
| 6,340,023 B2 | | 1/2002 | Elkins |
| 6,631,718 B1 | | 10/2003 | Lovell |
| 6,823,869 B2 | | 11/2004 | Raje et al. |
| 6,871,648 B1 | | 3/2005 | Winekoff |
| 7,080,645 B2 | | 7/2006 | Genger et al. |
| 7,343,917 B2 | | 3/2008 | Jones |
| 7,392,805 B2 | | 7/2008 | Maguire |
| 7,448,376 B2 | | 11/2008 | Lepel |
| 7,669,595 B1 | | 3/2010 | Mitchell |
| 7,836,885 B2 | | 11/2010 | Abrams |
| 8,042,536 B1 | | 10/2011 | Howey |
| 8,276,587 B2 | | 10/2012 | Zhang et al. |
| 8,365,734 B1 | | 2/2013 | Lehman |
| 8,517,017 B2 | | 8/2013 | Bowditch et al. |
| 8,517,023 B2 | | 8/2013 | Henry |
| 8,534,280 B2 | | 9/2013 | Dhuper et al. |
| 8,616,200 B2 | | 12/2013 | McKinnon |
| 2002/0046755 A1 | * | 4/2002 | De Voss ................. 128/207.18 |
| 2003/0024533 A1 | | 2/2003 | Sniadach |
| 2003/0172936 A1 | * | 9/2003 | Wilkie et al. ............ 128/207.18 |
| 2004/0016432 A1 | * | 1/2004 | Genger et al. ........... 128/204.18 |
| 2004/0035431 A1 | * | 2/2004 | Wright ................... 128/207.18 |
| 2007/0283957 A1 | * | 12/2007 | Schobel ............ A61M 16/0666 128/204.17 |
| 2008/0078382 A1 | | 4/2008 | LeMahieu et al. |
| 2008/0178875 A1 | | 7/2008 | Henry |
| 2009/0025723 A1 | * | 1/2009 | Schobel ............ A61M 16/0666 128/204.17 |
| 2009/0126723 A1 | | 5/2009 | Dhuper et al. |
| 2009/0209877 A1 | | 8/2009 | Zhang et al. |
| 2009/0260628 A1 | | 10/2009 | Flynn, Sr. |
| 2010/0170513 A1 | | 7/2010 | Bowditch et al. |
| 2010/0180891 A1 | | 7/2010 | McKinnon et al. |
| 2010/0252037 A1 | | 10/2010 | Wondka et al. |
| 2013/0032142 A1 | | 2/2013 | Neely |
| 2013/0032146 A1 | | 2/2013 | Neely |
| 2013/0032153 A1 | | 2/2013 | Neely |

OTHER PUBLICATIONS

Chums, Inc., Original Cotton Retainer, http://www.chums.com/category/cotton/product/original-standard, printed Apr. 2, 2013.

Scunci, Scunci No-Slip Grip Flat No-Slip Neutral Headwraps, 9mm, http://www.amazon.com/Scunci-No-slip-Grip-Neutral-Headwraps/dp/B001T8OEH2/ref=pd_bxgy_bt_img_y, printed Apr. 2, 2013.

Phillips Respironics, Respironics GoLife Swivel Tubing w/ Exhalation Port, http://www.cpapsupplyusa.com/Respironics-GoLife-Swivel-Tubing.aspx, printed Apr. 2, 2013.

Roscoe Medical, Crush-Resistant Supply Tubing, http://www.roscoemedical.com/default.aspx?page=item%20detail&itemcode=001306, printed Apr. 2, 2013.

\* cited by examiner

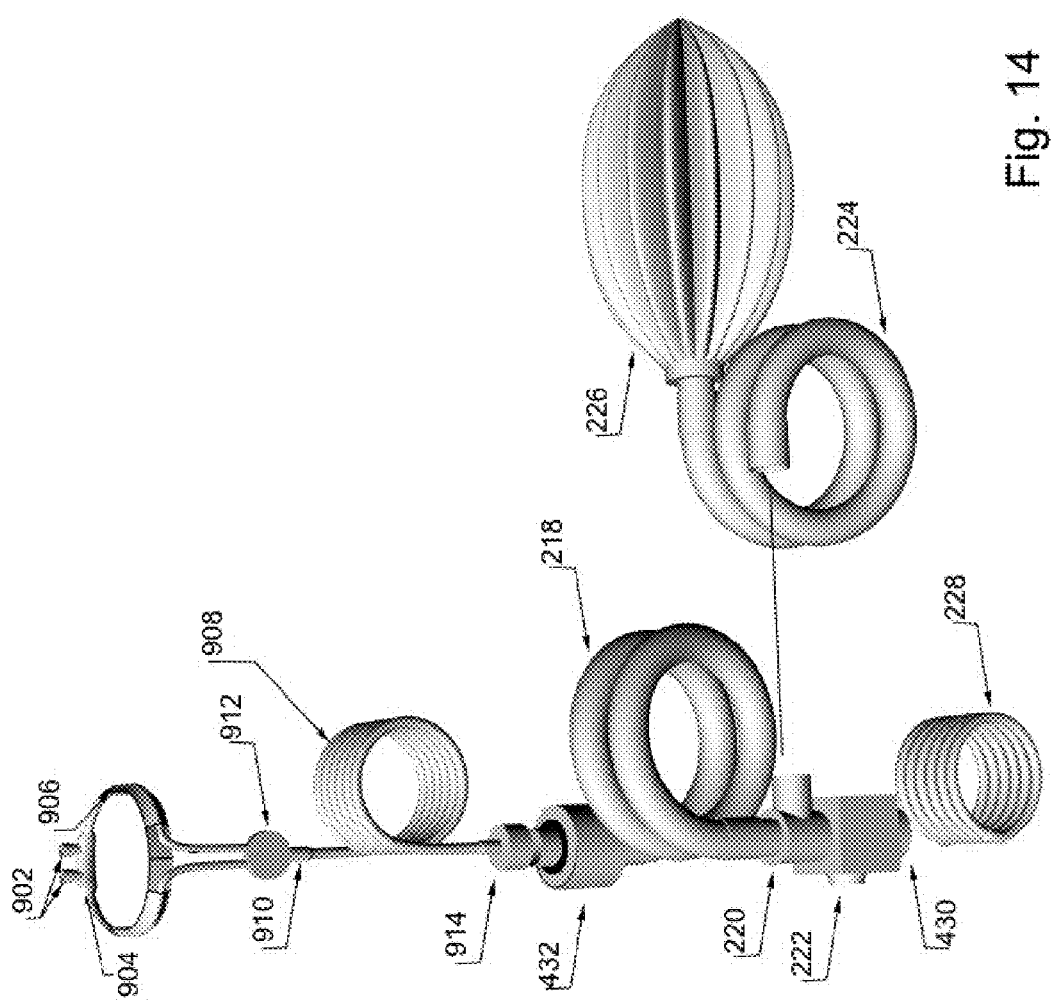

OXYGEN DELIVERY APPARATUS, SYSTEM, AND METHOD

CROSS-REFERENCE TO RELATED APPLICATION

This application claims the benefit of priority from U.S. Provisional Application No. 61/515,211 filed on Aug. 4, 2011, U.S. patent application Ser. No. 13/313,634 filed on Dec. 7, 2011, U.S. patent application Ser. No. 13/313,707 filed on Dec. 7, 2011, and this is a continuation-in-part of U.S. patent application Ser. No. 13/313,559 filed on Dec. 7, 2011.

FIELD OF THE DISCLOSURE

The disclosure relates to apparatus, systems, and methods for delivering oxygen to a user. The disclosure also relates to the delivery of air to a user through a mask.

BACKGROUND

For someone facing a life altering or even life ending trauma or disease, every opportunity afforded them for healing or life extending treatment is a blessing. Sometimes these treatments cost thousands or even millions of dollars. And some of these treatments, as is the case of oxygen therapy, can be very uncomfortable to administer, even painful. The equipment used to administer oxygen can cause sores on the face, rub the skin raw, and dry out the lips, nose, and mouth to the point of cracking and bleeding. This equipment frequently causes panic attacks due to the lack of reserve oxygen capacity with just mild exertion; or it can make an already severe panic attack worse. The design of the mask has remained virtually unchanged since its creation; a single rubber band strap to secure a molded silicone "one size fits all" face piece into place. This leaves very little room for adjustment and makes for a highly inefficient delivery system. Add to these limitations the fact that oxygen tanks are bulky, heavy and limited in their capacity, or restrictive to the mobility of the user.

Most people today live with an oxygen level in the upper 90s as a percentage of oxygen saturation of the blood. Oxygen levels lower than approximately 92% mean that the red blood cells are starving for oxygen. For nearly all patients utilizing an oxygen mask, a dip in O2 saturation below this level will trigger a panic attack. Most of these patients are then required to take prescription anti-panic medication to minimize the effects of these attacks. This, in turn, can alter the mental state of the patient and further decrease quality of life. Frequent decreases in O2 saturation can have devastating effects on the body. Even a minor decrease in oxygen saturation to the brain can start the initial stages of Cerebral Hypoxia—literally 'brain death'—where brain cells immediately begin to die off. The effects of cerebral hypoxia are severe and can happen rapidly upon loss of oxygen. Some of those effects in mild cases are poor judgment, inattentiveness, lack of coordination, and memory loss. In severe cases the effects may include permanent brain damage, coma, lung infections, pneumonia, blood clots, seizures, and death.

In some cases, a patient may use cannulas which provide oxygenated air to the patient's nostrils. Cannulas utilize narrow tubing under the patient's nose with holes placed under each nostril. In some devices, the holes are within a protrusion or extension directed generally toward the nostrils. Both versions of cannulas provide the oxygenated air at a velocity that is fast enough to limit dissipation of the oxygenated air into the ambient. The lower the velocity of air used, the more air that may dissipate into the ambient instead of into the patient's pulmonary system. However, the increased velocity of air may cause discomfort to the patient by drying out their nostrils, among other irritations. In addition, placement of such cannulas may require significant amounts of adhesive materials and/or periodic repositioning, irritating the patient. Any discomfort or irritation in wearing the cannula or caused by the airflow of the cannula may cause a patient to forgo beneficial use of the oxygenated airflow.

SUMMARY

This disclosure presents devices that may be incorporated into a system for the improved delivery of oxygen to a person. The disclosure further presents a method of using the system for improved oxygen delivery. Embodiments of the disclosed apparatus, system, and method may provide for one or more of the following: improved comfort for the user, eliminating or minimizing the chafing of the user's skin, lower oxygen use, increased efficiency in oxygen use, simplified operation and monitoring, and improved quality of life for a user.

Embodiments of the disclosure may include one or more of the following: a strap that does not pull on hair or rest on the ears, larger tubing closer to the face for better oxygen delivery, and a large reserve of oxygen. In addition, embodiments of the system may be designed to only give oxygen when the patient needs it, to alert a caregiver if the mask comes off, and/or create a tight seal and good positive pressure for every breath the patient takes without causing panic.

Some embodiments of the disclosure include an air delivery system having a mask, a flow rate throttling valve, and an air source. During operation the mask covers at least one of the user's mouth or nose and is operatively associated with a user's breathing. Operatively associated with the mask is the flow rate throttling valve, which facilitates the flow of air to the mask, and allows a constant minimum flow rate while varying the flow rate to maintain a positive pressure. The flow rate throttling valve is also operatively associated with the air source.

Some embodiments of the disclosure include a mask for an air delivery system that has a mask body that covers the mouth and nose of a user. The mask body defines an interior cavity between the face of the user and said mask body. The mask body includes a contact edge, an input port, an exhaust port, and an access port. The contact edge abuts the face of said user during operation. The air in the system is delivered to the user through the input port, and exhaled air from the user may exit the mask through the exhaust port. The access port allows access to the interior cavity defined by the mask body and the user's face and may be at least partially sealed.

Some embodiments of the disclosure include an air modification module for an air delivery system which has a sealable container and a cartridge. The sealable container is operatively associated with the air delivery system and may be connected in the path of airflow towards a user. The sealable container has an airflow input and an airflow output, and airflow within the air delivery system may enter the airflow input and exit the airflow output. The cartridge may be within the sealable container, and may modify the airflow by providing particulate material into the airflow. In some embodiments, there are a plurality of replaceable cartridges.

Some embodiments of the disclosure include an air delivery system having a mask, an air modification module, a flow rate throttling valve, an air source, an air reservoir, and a coupling. The mask is operatively associated with a user's breathing during operation of the air delivery system. The air modification module is operatively associated with the mask, and modifies air content within said air delivery system during operation. The flow rate throttling valve is also operatively associated with the mask, and facilitates the flow of air to the mask. The air source is operatively associated with the flow rate throttling valve and provides a source of air, or in some embodiments conditioned air. The air reservoir is also operatively associated with said mask, and may be used to alter the flow of air to the mask. For example, the air reservoir may be used to force air into a patients pulmonary system. The coupling is operatively associated with the mask, the flow rate throttling valve, and the air reservoir, and directs airflow through the air delivery system towards at least one of said air reservoir and said mask.

Some embodiments of the disclosure include a harness for a mask having a headpiece, a strap, and at least one ear piece. The strap is operatively associated with the headpiece and the mask, and includes the ear piece and the mask connector. The ear piece is designed to fit around a user's ear and has a headpiece side and a mask side. The ear piece is sufficiently rigid to transfer force between the headpiece side and the mask side. The mask connector attaches the harness to the mask.

Some embodiments of the disclosure include a sensor system for an air delivery system having an airflow sensor and a response system. The airflow sensor detects airflow characteristics within the air delivery system. The response system generates an output based upon the detected airflow characteristics. The out put is may be a visual alert, an audible alert, an electronic signal, and/or a mechanical action.

Some embodiments of the disclosure include a mask for an air delivery system having a contact edge, an input port, and an exhaust port. The contact edge abuts the face of the user during operation. The contact edge also includes a contact sensor that detects a change in pressure between the contact edge and the face of the user, and provides an indication of the change in pressure. The air from the air delivery system is delivered to a user through the input port, and exhaled air from the user may exit said mask through the exhaust port.

Some embodiments of the disclosure include a cannula for an air delivery system having a velocity reduction compartment and nostril fittings. The velocity reduction compartment may include one flat, semi-flat, or contoured side whereby such side is adjacent to the skin of the user and limits the cannula's ability to rotate, and increases comfort to the user. The nostril fitting may include a replaceable sleeve that is removably attached to the cannula and fits a nostril such that the cannula is in a sealed or semi-sealed connection with the patient's nostril. Some embodiments of the cannula may further include moldable components associated with one or more portions of the tubing, whereby molding the component to the corresponding physical features of a patient may limit movement of the cannula and tubing therefore. The air from the air delivery system is delivered to a user through the cannula input tubing. In some embodiments of the cannula, the cannula input tubing may be associated with a strap that fits around a patient's head and maintains the cannula input tubing above the patient's ears.

Additional aspects, advantages and features of the present invention are included in the following description of exemplary examples thereof, which description should be taken in conjunction with the accompanying figures, wherein like numerals are used to describe the same feature throughout the figures.

A BRIEF DESCRIPTION OF THE DRAWINGS

Figure 2:
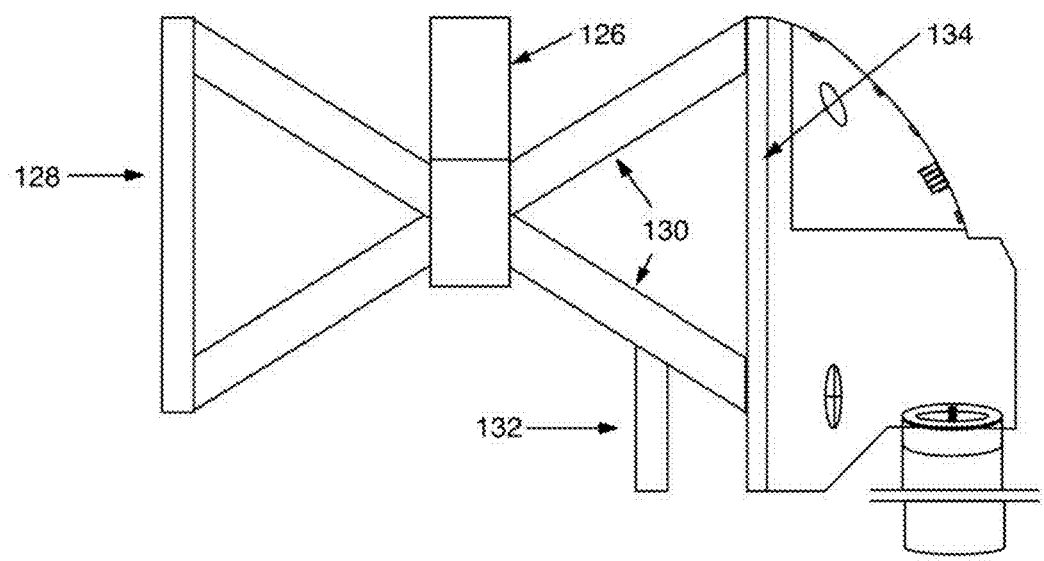
Figure 3:
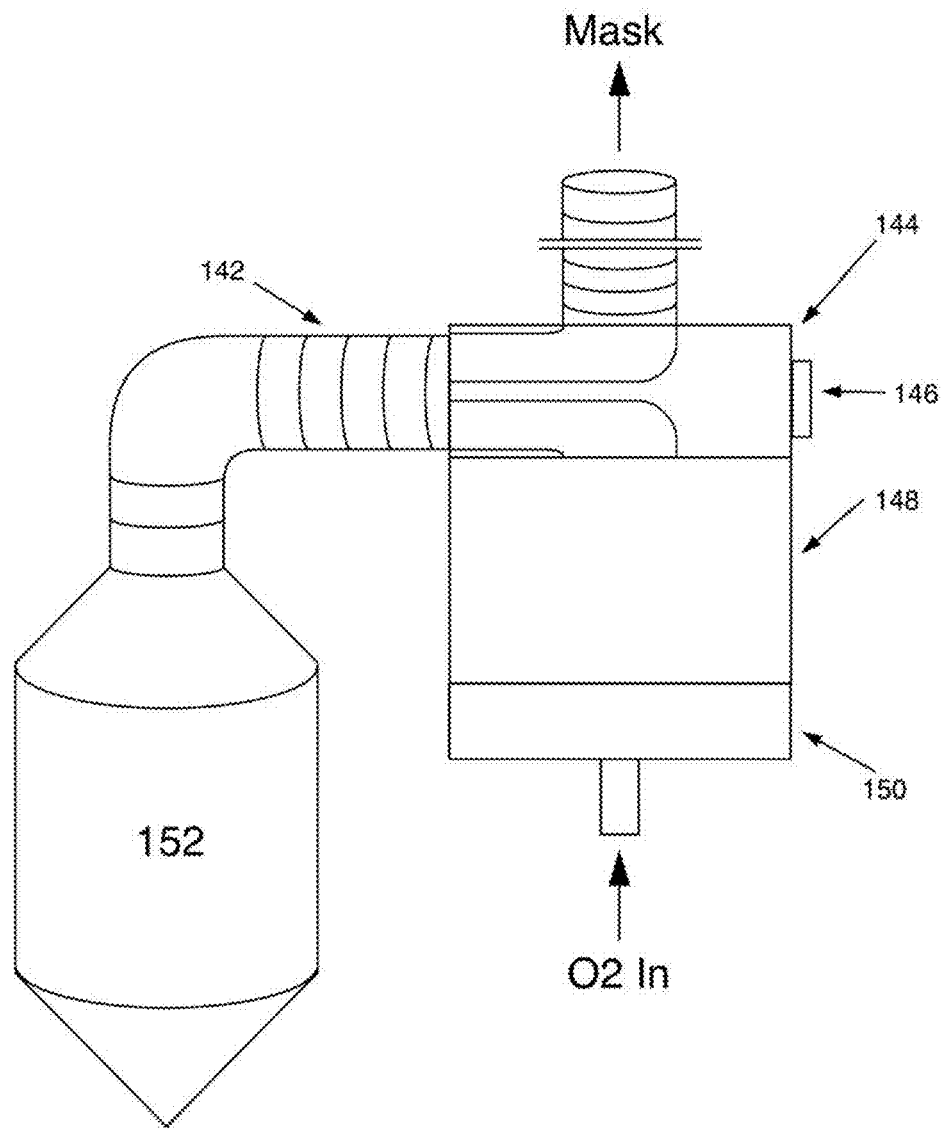
Figure 4:
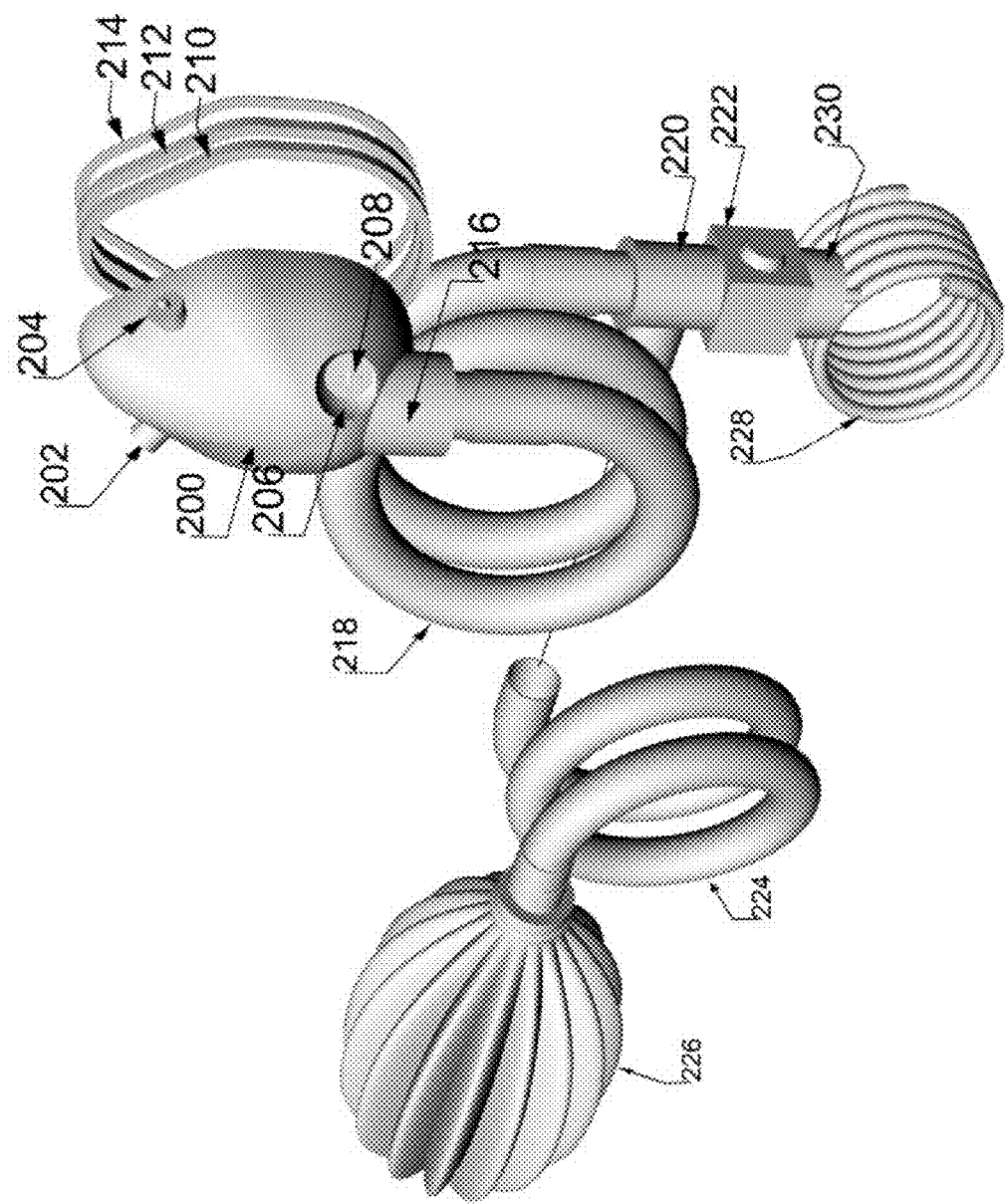
Figure 5:
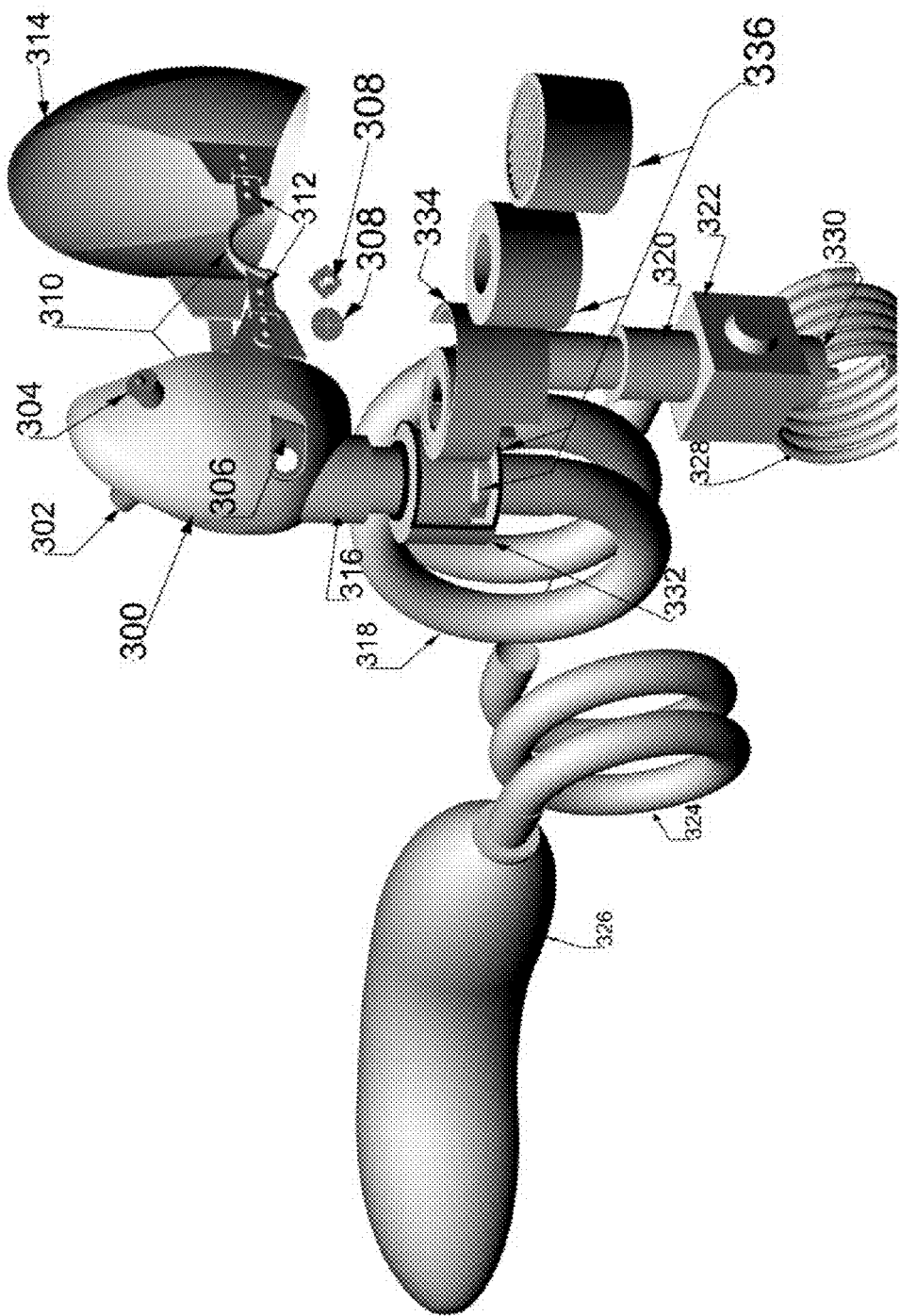
Figure 6:
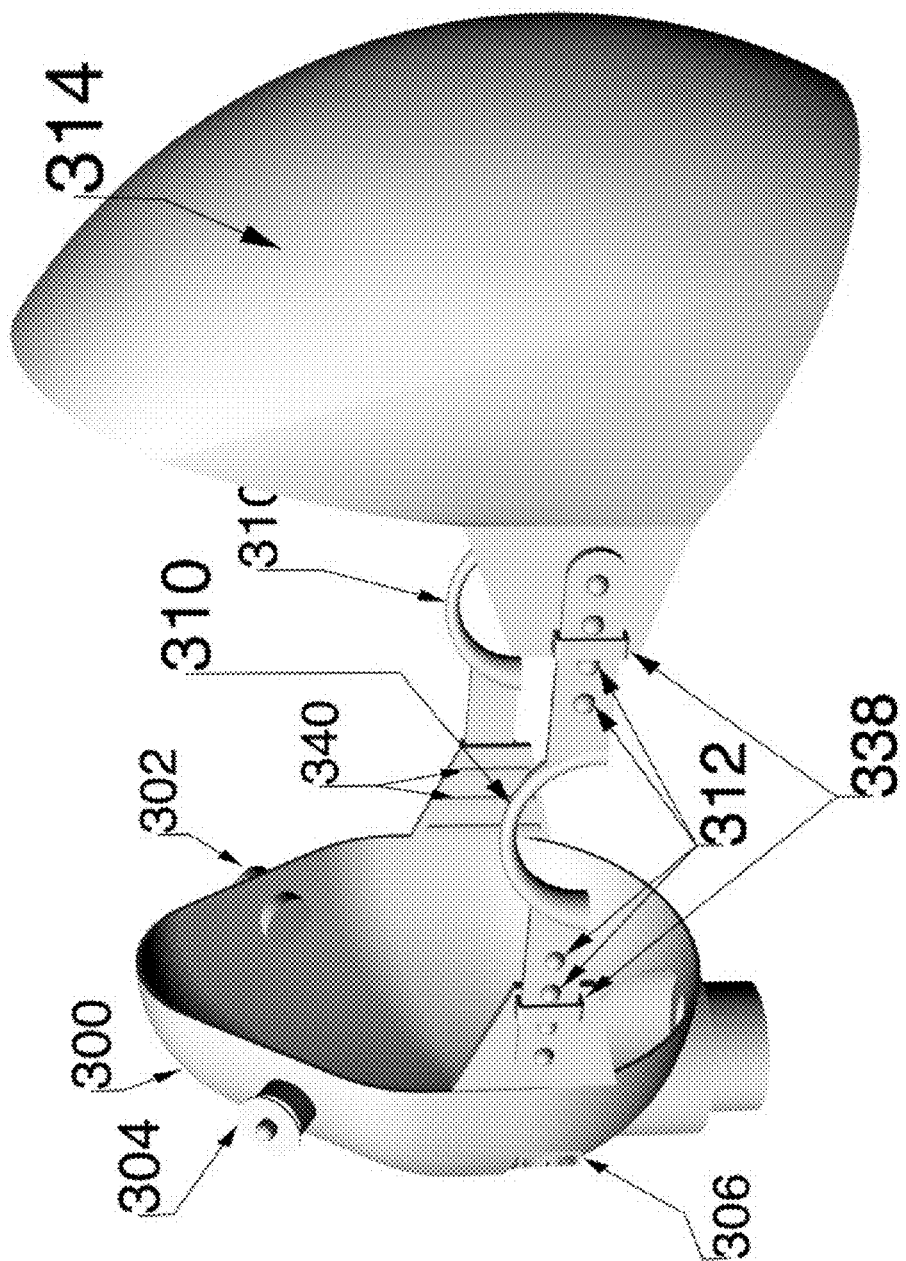
Figure 7:
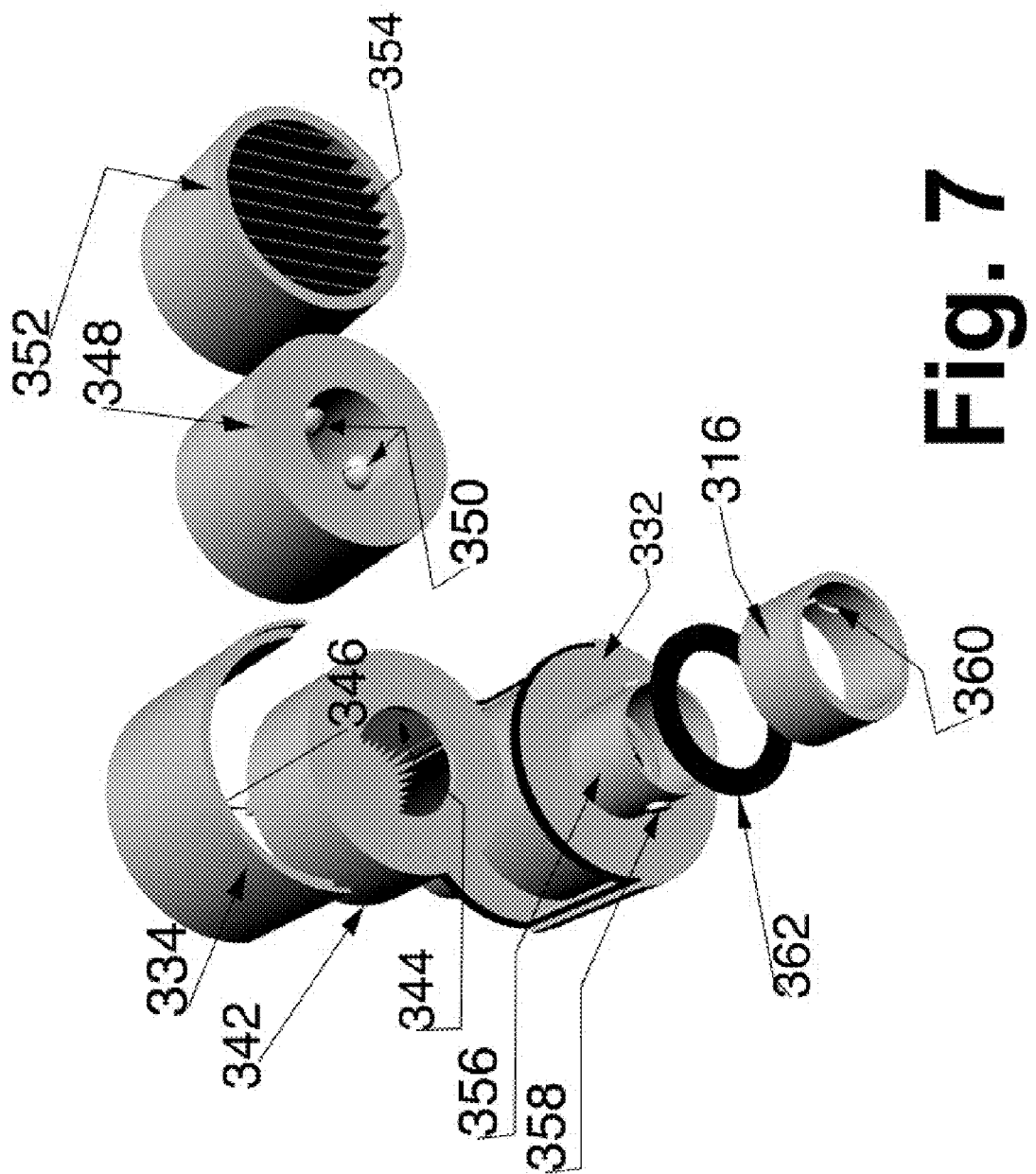
Figure 8:
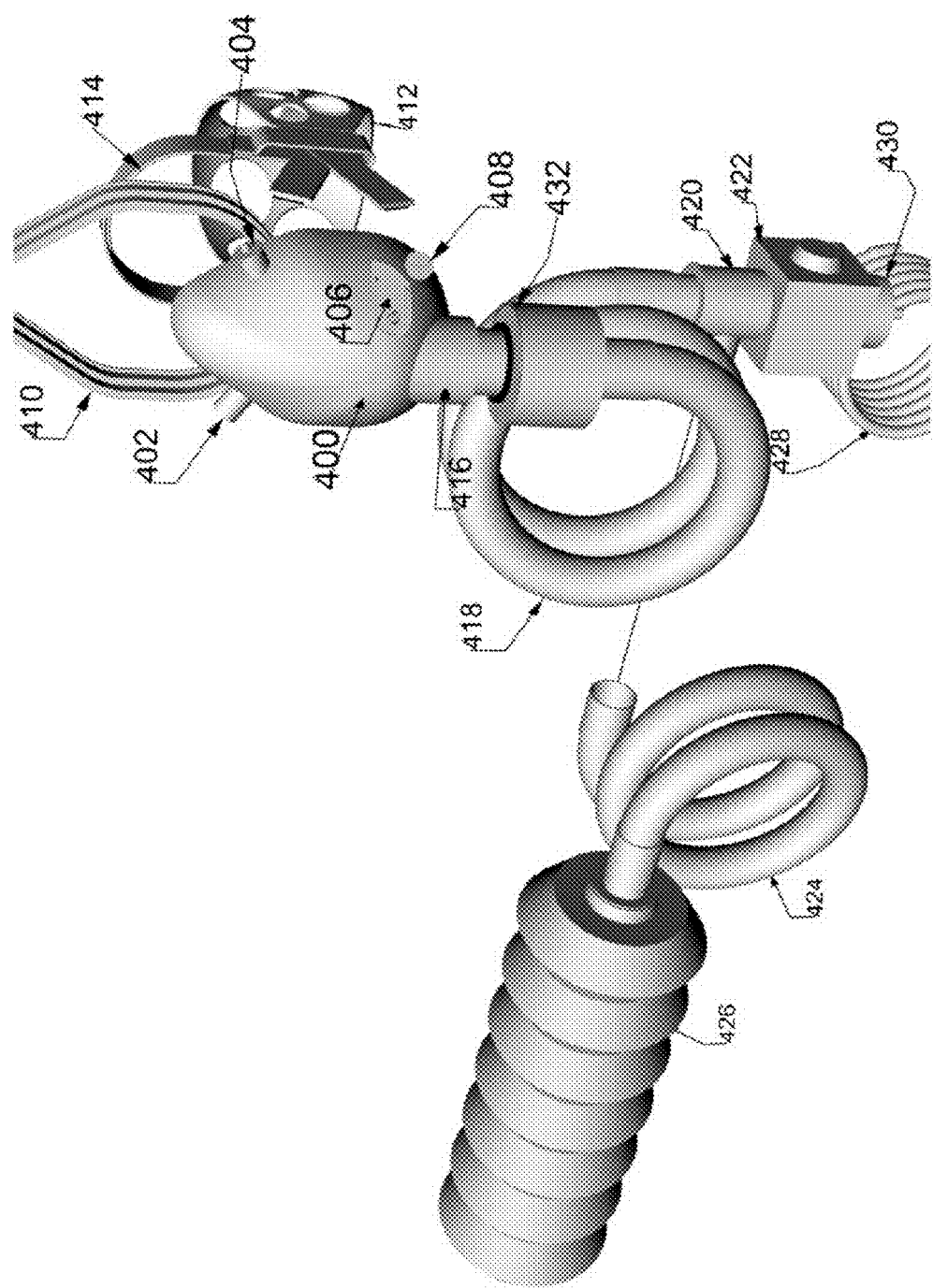
Figure 9:
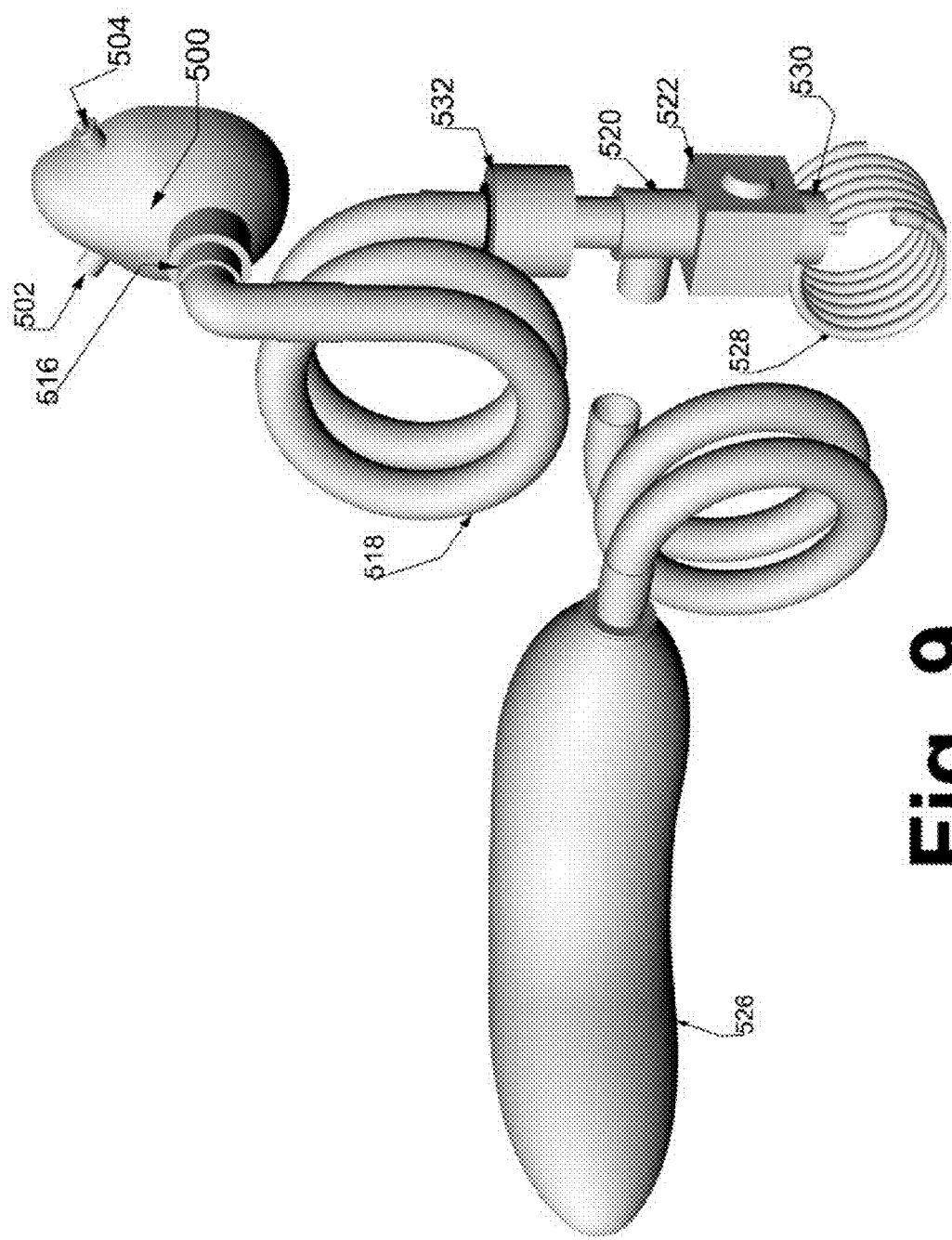
Figure 10:
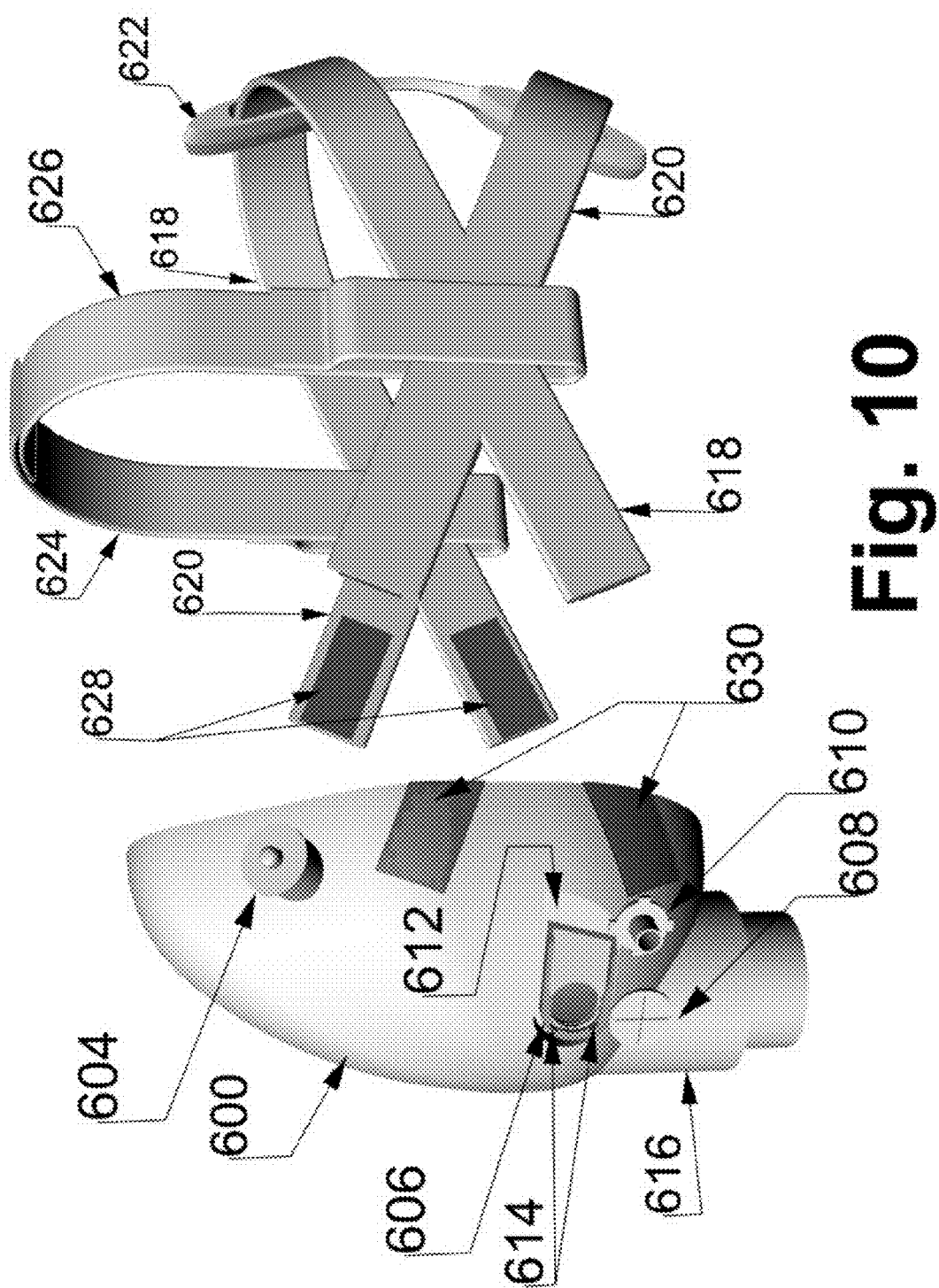
Figure 11:
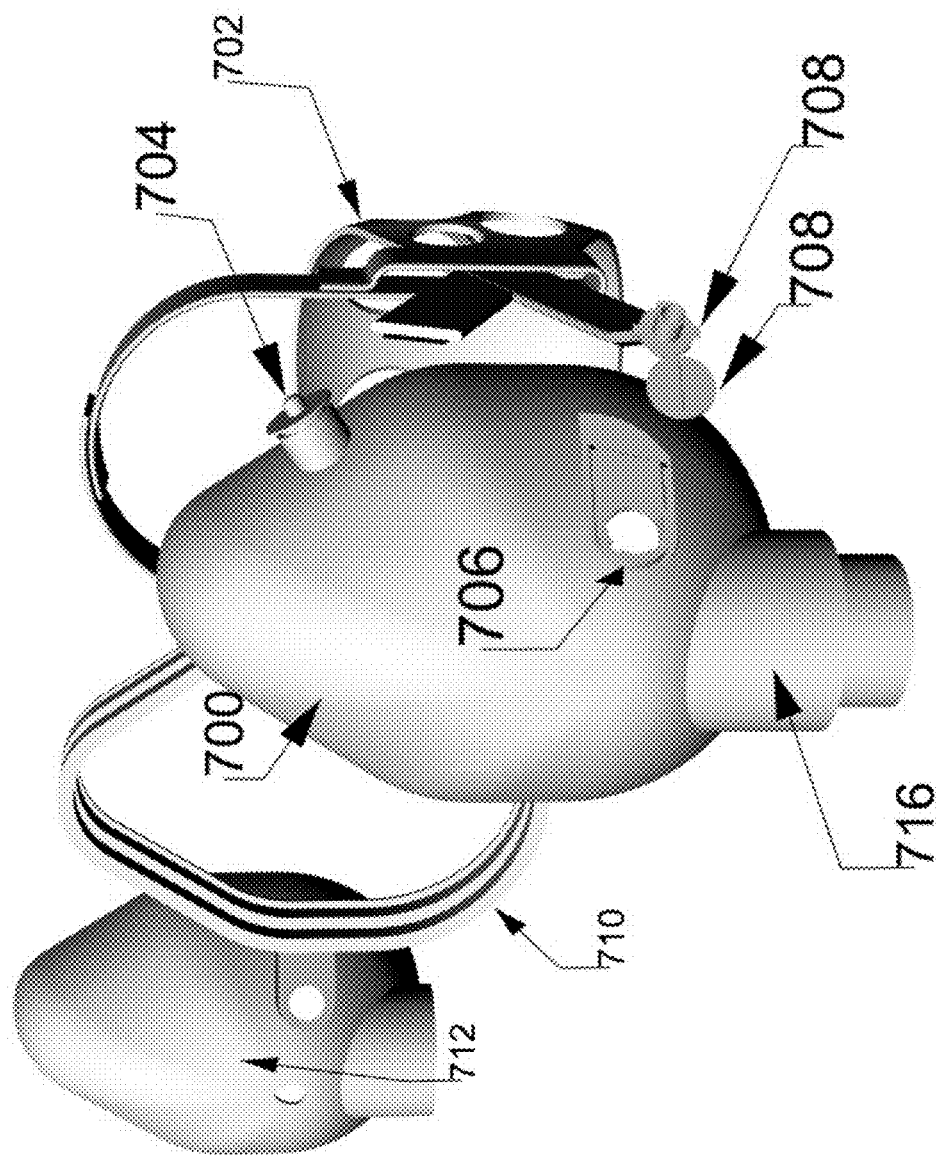
Figure 12:
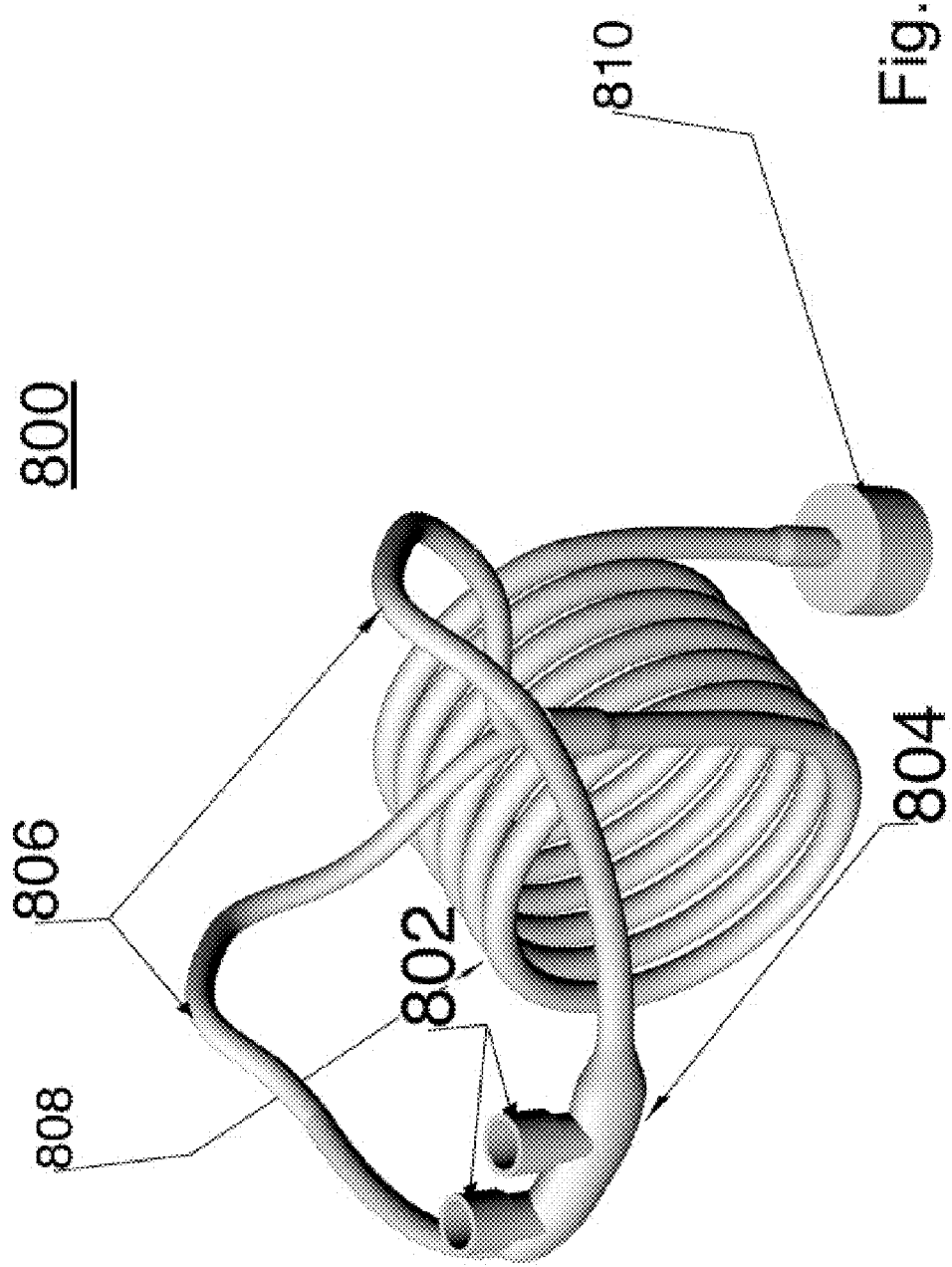
Figure 13:
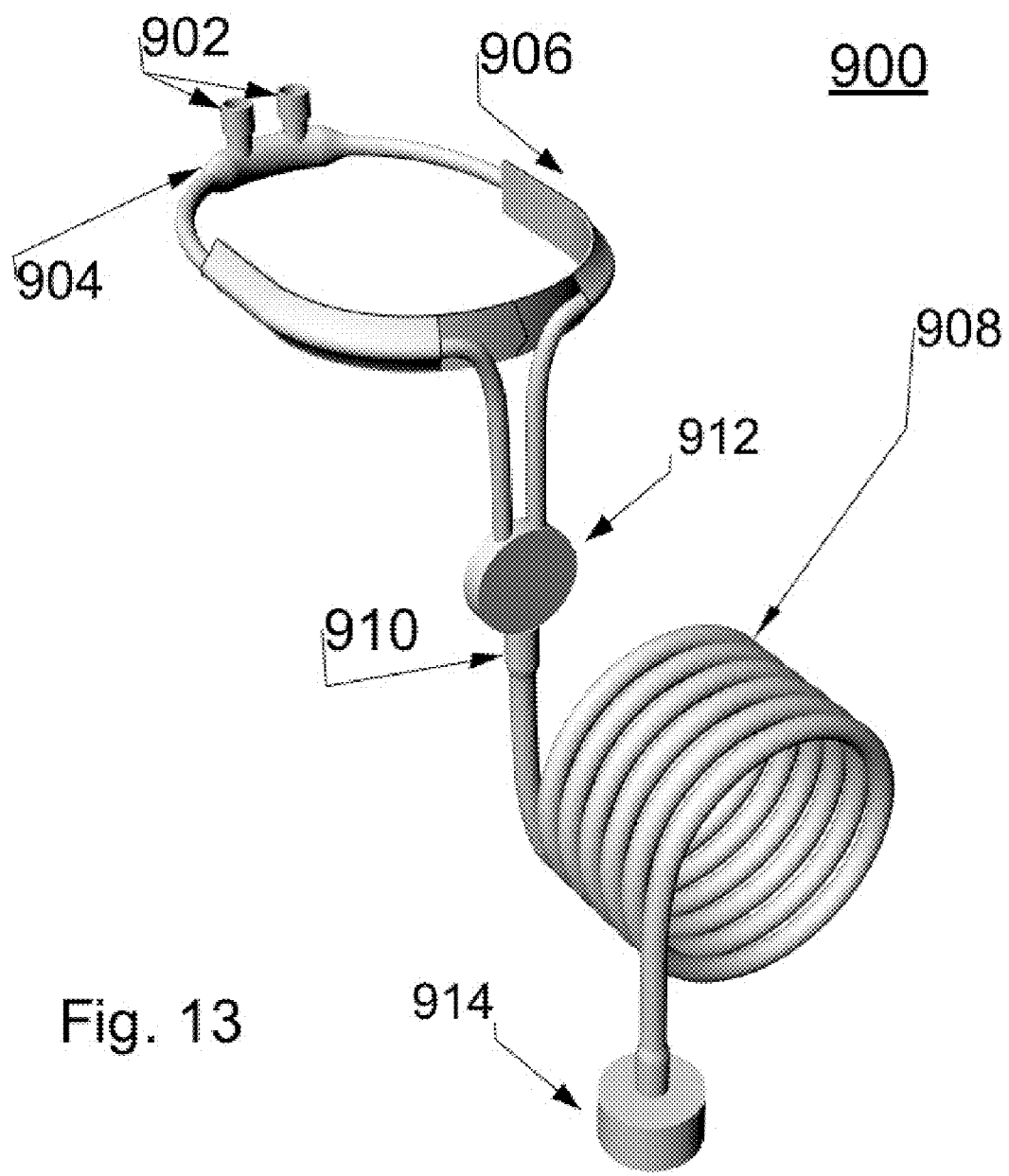

FIG. 1 is a view of a mask from a behind view;
FIG. 2 is a side view of a mask and harness;
FIG. 3 is a schematic depiction of an O2 supply system;
FIG. 4 is a depiction of an embodiment of an air delivery system;
FIG. 5 is a depiction of another embodiment of an air delivery system;
FIG. 6 is a depiction of another embodiment of a mask and harness;
FIG. 7 is a depiction of an air modification module;
FIG. 8 is a depiction of another embodiment of an air delivery system;
FIG. 9 is a depiction of another embodiment of an air delivery system;
FIG. 10 is a depiction of another embodiment of a mask and harness;
FIG. 11 is a depiction of another embodiment of a mask and harness with a sanitary sheet;
FIG. 12 is a depiction of an embodiment of a cannula and cannula input tubing;
FIG. 13 is a depiction of another embodiment of a cannula and cannula input tubing with a head strap; and
FIG. 14 is a depiction of another embodiment of a cannula in operative association with an air delivery system.

DETAILED DESCRIPTION

The following is a legend of the references used in FIGS. 1 and 2:
Strap Connectors 102, 104, 106, and 108;
O2 input port 110;
Back flow preventer 112;
Exhaled Air Removal Flap 114;
Safety Valve 116;
Exhale exhaust port 118;
Exhale flap spring 120;
Access port 122;
Input port tubing 124;
Overhead strap 126;
Back of head strap separator 128;
Crossed straps 130;
Chin strap 132; and
Molding strip 134.
The following is a legend of the references used in FIG. 3:
Large-diameter tubing 142;
Throttling valve output coupling 144;
Attention alarm connector 146;
Flow rate throttling valve 148;
Moisture additive box 150; and
Reserve air reservoir 152.
The following is a legend of the references used in FIG. 4:
Mask 200;
Exhale valve 202;
Safety valve 204;
Access port 206;
Access port seal 208;
Molding ring 210;
Skin sensor ring 212;
Contact ring 214;
Input port 216;
Input port tubing 218;
Output coupling 220;
Flow rate throttling valve 222;
Reservoir tube 224;
Air reservoir 226;
O2 input tube 228; and
Air modification module 230.
FIGS. 1 and 2 show an embodiment of a mask. FIG. 1 shows a mask from a behind view wherein the view is from the user's direction to the mask. FIG. 2 shows a mask with the harness for attaching the mask to a user's head. Other than stated herein, the mask may be made of the same materials currently used in masks.

The mask includes strap connectors 102, 104, 106, and 108. Strap connectors 102, 104, 106, and 108 are where the crossed straps 130 connect to the mask.

The mask further includes an O2 input port 110 that connects the mask with a source of oxygen through other system components described further below. This embodiment of O2 input port 110 includes a back flow preventer 112 shown in the center of O2 input port 110. O2 input port 110 is large to provide quiet operation. For example, in some embodiments O2 input port 110 may be ½ inch in diameter and in other embodiments O2 import port may be 1 inch in diameter. Oxygen will flow through O2 input port 110 at a slower velocity due to the larger size of O2 input port 110 over existing systems. The shape and/or material of O2 input port 110 may be varied to help dampen the sound of the oxygen flowing. For example, O2 input port 110 may be made of a material that will dampen (or filter) the frequencies of the air noise but not inhibit the frequencies of voice which will help people to hear the patient talk.

The mask also includes an exhaled air removal flap 114. This exhaled air removal flap 114 pushes unwanted exhaled breath out of the mask. Removal of the exhaled breath reduces the successive rebreathing of the same air and improves the efficiency of delivering the desired air content to a user. In addition, the mask includes safety valve 116. In case of O2 flow loss for any reason, safety valve 116 will open allowing patient to breathe fresh air. The mask also includes exhale exhaust port 118 located in exhaled air removal flap 114. Exhale exhaust port 118, operates as a vent port which is designed to efficiently exhaust the unwanted exhaled air that remains in existing masks with every breath. Exhaled air removal flap 114 is attached to the mask by exhale flap spring 120. Exhale flap spring 120 is used to trigger exhaled air removal flap 114 which pushes exhaled air out of the mask to be replaced by O2 rich air from O2 input port 110 of the mask.

In this embodiment, the mask includes access port 122. Access port 122 is a self shutting port which may be used for inserting a straw for drinking, to administer medicine, or for other uses which may be apparent to those skilled in the art. Access port 122 may be a covered vent/flap close to the mouth opening to give the patient a place to put a straw through, to take a temperature or administer drugs.

The mask includes input port tubing 124 connected to O2 input port 110 to provide oxygen rich air to the user. Input port tubing 124 may be flexible but collapse resistant, and include air flow noise reducing characteristics. These characteristics may be incorporated by either by type of material or design of the tubing used for input port tubing 124.

The mask includes a harness to secure the mask around a user's head and in proper position over the person's mouth and nose. In the embodiment shown, the harness that holds the mask on a user's head will be connected to the mask by no less than 4 points on the mask. One skilled in the art will recognize that the number of contact points for attaching the harness and minimizing slip and chafing may vary and remain within the scope and spirit of the invention. This harness may be made of material that is soft and has a large surface area to distribute the forces as equally as possible around the head. The harness may also include a mechanism to prevent the harness from resting on the user's ears to prevent chafing.

The harness includes an overhead strap 126 that is adjustable and used relieve the pressure of the crossed straps 130 positioned over the ear and to give more comfort to a user. The harness also includes back of head strap separator 128 that is a spacer that forces the crossed straps 130 apart allowing better distribution of the forces on the head. Crossed straps 130 are designed from a flexible material to provide tension to hold the mask in place upon a user's head. Crossed straps 130 cross above the ear and adjust to allow slightly upward angular force to the strap that connects close to the bottom of the mask and a slightly downward angular force to the strap that connects close to the top of the mask. Crossed straps 130 may be made of a soft material and may be extra wide to give more comfort to a user. Finally, the harness may include a chin strap 132 used to put a slight upward force on the chin to help force the mouth of the patient closed. One skilled in the art will recognize that chin strap 132 may be removable because it may not be needed all the time. Some embodiments of the harness may not include chin strap 132.

Some embodiments of the mask include a molding strip 134 that surrounds the entire opening of the mask. Molding strip 134 may include a skin contact sensor system made up of one or more skin contact sensors used to detect mask missalignment or removal. The skin contact sensors may be made with discrete electrical components. The skin contact sensors may utilize a limited power source associated with the detection system only. Alternatively, the skin contact sensors may receive sufficient power from a remote power source associated with the detection system. The skin contact sensors may be used to send a signal if the mask comes off for any reason.

Molding strip 134 may also be designed to be form molded to improve the mask's fit to the patient's face to create a tight seal and improve comfort for a user. The design may allow for molding strip 134 to be form molded by hand or using tools. In addition, the materials that make up molding strip 134 may have anti-slip properties to prevent the mask from moving around and to prevent or minimize chafing of the skin.

Molding strip 134 provides a tight fit that is molded to the contours of the human face. In some embodiments, molding strip 134 uses aluminum adjustment rods all the way around it to insure that it keeps its shape. This will also insure that the mask does not move around on the face and chafe the skin. One skilled in the art will recognize that the mask may include materials and/or designs around the edge to provide additional padding and comfort while preventing or minimizing slip.

FIG. 3 shows an embodiment of an oxygen supply system for the mask. Other than stated herein, the oxygen supply components may be made of the same materials currently used in air supply systems.

In this embodiment, the oxygen supply system uses large-diameter tubing 142 that goes from the reserve air reservoir 152 to the flow rate throttling valve output coupling 144. In other embodiments, the large-diameter tubing 142 may be moved to the input side of the flow rate throttling valve 148.

In this embodiment, throttling valve output coupling 144 connects the mask's O2 input port 110 to the flow rate throttling valve 148 through flexible tubing (referred to as input port tubing 124 in FIG. 1), and also connects the reserve air reservoir 152 via the large-diameter tubing 142. In some embodiments, the length of flexible tubing is designed to help move other components away from the mask. For example, flexible tube may be at least 1.5 feet in length to help move the other components away from the mask. In addition, this tube will also be made to reduce oxygen flow noise. In some embodiments, the flexible tubing is the same diameter as O2 input port 110 of the mask. The flexible tubing will include anti-collapsing characteristics to prevent loss of airflow to the user.

Throttling valve output coupling 144 also includes a flow director that forces O2 to flow into the reserve air reservoir 152. The air may then come out of the reserve air reservoir 152 and up to the mask. In some embodiments, an attention alarm connector 146 may be attached to the flow rate throttling valve output coupling 144. The patient may press attention alarm connector 146 to provide an alarm to get the attention of the caregiver. Alternatively, attention alarm connector 146 may provide an alarm to a caregiver if a malfunction in the oxygen supply system is detected.

Flow rate throttling valve 148 conserves O2 use by limiting the O2 supply to when it is needed and minimizes the flow of O2 when it is not needed. Flow rate throttling valve 148 also functions in such a way that it regulates the pressure on the output side of flow rate throttling valve 148 (going to the mask) to be as close to 0 psi (but still positive) as possible, thus preventing a vacuum (negative pressure) on the output side of flow rate throttling valve 148. Flow rate throttling valve 148 also acts as a backflow preventer (check valve) insuring that exhaled air goes out exhale exhaust port 118 (FIG. 1) in the mask. In some embodiment, flow rate throttling valve 148 is mechanical. In other embodiments, flow rate throttling valve 148 is electronic. Flow rate throttling valve 148 will also include an indicator showing a rate of flow. In some embodiments, the indicator will not be a gauge for accurate measurement, will show that flow rate throttling valve 148 is functioning and/or the patient is breathing on their own. In some embodiments, the indicator will be electronic.

The output of flow rate throttling valve 148 will be forced by a directional port into reserve air reservoir 152. This will give a buffer to flow rate throttling valve 148 to help reduce the possibility that the patient feels like they have to draw in each breath.

In some embodiments, reserve air reservoir 152 may be installed on the input side of flow rate throttling valve 148 to insure that reserve air reservoir 152 keeps full at all times. Flow rate throttling valve 148 will provide an increased efficiency of the oxygen delivery system. With flow rate throttling valve 148 in place, the flow rate going into this system from the oxygen source may be increased dramatically to insure higher reserve oxygen in reserve air reservoir 152 or to not use the reserve all together. The increased flow rate will also help the input oxygen lines from kinking and collapsing.

Moisture additive box 150 will be used to mix the O2 with either water vapor or medicine to prevent drying out the nasal passages and mouth of the patient. In this embodiment, moisture additive box 150 is located at the input to flow rate throttling valve 148, but one skilled in the art will recognize that the location of moisture additive box 150 may vary. In this embodiment, the O2 source is connected to the input for moisture additive box 150. The O2 source may be any type of oxygen source, such as an O2 tank or regulator.

The oxygen supply system includes reserve air reservoir 152 which may be a reserve capacity bag or very flexible container designed to hold oxygen. In cases of extreme exertion a user may utilize the reserve O2 supply in reserve air reservoir 152. Reserve air reservoir 152 may be connected by large-diameter tubing 142 to either the input side or the output side of flow rate throttling valve 148. Reserve air reservoir 152 will be flexible and as flat as possible to prevent it from "getting in the way" of the patient. In addition, reserve air reservoir 152 must be flexible enough to insure that if the patient oxygen volume requirements exceed the maximum available, reserve air reservoir 152 does not create a negative pressure on the output side of flow rate throttling valve 148.

In some embodiments, reserve air reservoir 152 will also give the caregiver or patient the ability to force the reserve air into the patient's lungs at a higher pressure than normal by simply squeezing reserve air reservoir 152. In such embodiments, reserve air reservoir 152 must also be strong enough to withstand being squeezed to provide life sustaining positive pressure on the output port (or into the mask). For example, reserve air reservoir 152 may be used as a ventilator bag and/or to reduce the burden on the patient in drawing a breath.

In the embodiment shown, reserve air reservoir 152 is shown as a two liter reservoir, but one skilled in the art will recognize that the volume of reserve air reservoir 152 may vary. For example, reserve air reservoir 152 may hold one liter of oxygen by volume.

In this embodiment, the oxygen delivery system may be used by securing the mask over a user's face using the harness. The mask may be molded to the user's face using molding strip 134. The oxygen source provides an O2 flow through moisture additive box 150 into flow rate throttling valve 148. The O2 continues through throttling valve output coupling 144 into reserve air reservoir 152 via large-diameter tubing 142. During the user's breathing cycle, the user may inhale O2 from reserve air reservoir 152 via large-diameter tubing 142 and throttling valve output coupling 144. From throttling valve output coupling 144 the O2 travels through input port tubing 124 into the mask. During inhalation, air travels into the mask through O2 input port 110 and continues into the user's respiratory system. During exhalation, air travels out of the user's respiratory system into the mask and is prevented from returning through O2 input port 110 by the back flow preventer 112. Instead air is expelled through exhale exhaust port 118. Exhaled air may also be expelled by exhaled air removal flap 114 which may be triggered by exhale flap spring 120.

FIG. 4 shows an embodiment of an oxygen delivery system of the disclosure. Mask 200 is designed to fit a user's face, covering the nose and mouth of a user. Mask 200 allows a user to breathe normally while providing conditioned air content, such as air with an increased O2 level. In this embodiment, mask 200 includes exhale valve 202, safety valve 204, and access port 206.

Exhale valve 202 shown in this embodiment provides a means for exhaled gas to exit mask 200 and minimize the potential for a user to re-breathe exhaled air. Exhale valve 202 may be designed in a number of manners for removing a user's exhaled breath. For example, exhale valve 202 may include a flexible seal that opens to the ambient based upon pressure from a user's exhalation, allowing exhaled air to disperse to the ambient, while the flexible seal prevents (or minimizes) entrainment of air from the ambient based upon pressure caused by a user's inhalation. One skilled in the art will recognize that other valves for allowing exhaled air to disperse to the ambient may be implemented and remain within the scope and spirit of the present disclosure.

In addition, exhale valve 202 may be a removable element to allow replacement with another exhale valve 202 or alternative component. In some embodiments, exhale valve 202 may be replaced with a plug or seal if exhale valve 202 is unnecessary. Exhale valve 202 may be removable based upon any type of sealed connection. For example, exhale valve 202 may be connected to mask 200 by a threaded connection, a friction connection, a pressure connection, an adhesive connection or any other connection or combination of connections. A replaceable exhale valve 202 may be beneficial for improving sanitary conditions of the mask and/or operation for the user.

Safety valve 204 is shown in this embodiment opposite of exhale valve 202 in the top of mask 200. Safety valve 204 may be designed in a variety of embodiments. In some embodiments, safety valve 204 may be a mechanical valve that actuates based upon pressure in mask 200. For example, safety valve 204 may include a diaphragm whereby increased pressure on the diaphragm from an exhaled breath causes the diaphragm to open safety valve 204 to release the exhaled breath, and the diaphragm returns to it initial position once the pressure from the exhaled breath is released. In some embodiments, safety valve 204 is a sensitive valve that operates under low pressures. Operation under low pressure may be beneficial for users with weak breathing characteristics.

In some embodiments, safety valve 204 includes electronic components. Such components may operate a solenoid driven valve based upon timing or pressure detections, such as detections from an airflow sensor. In some embodiments with electronic components, safety valve 204 may be designed to actively exhaust air from mask 200 through suction or other means in order to minimize re-breathing of successive breaths. Electronic components may include a microcontroller to operate safety valve 204. Electronic components may also include a pressure sensitive device that measures the pressure in mask 200 to control flow rate throttling valve 222 and/or safety valve 204. In addition, such a pressure sensitive device may store and/or output pressure measurements for monitoring a users breathing.

In some embodiments, safety valve 204 may include an open and a closed state, where in the open state the valve is intended to allow exhaled gas to escape mask 200, and in the closed state the valve minimizes the release of gas to limit a bleed-off of the conditioned air intended for the user. In some embodiments, the closed state may not create an air-tight seal and will allow a flow-rate for exhaled air to escape. Such a design would allow exhaled air to escape even if there is a malfunction in the valve's operation. Some embodiments may be designed such that safety valve 204 returns to an open state if any malfunction occurs.

In some embodiments, safety valve 204 may address the functions of exhale valve 202 and allow for embodiments that do not include exhale valve 202. For example, exhale valve 202 may be unnecessary for embodiments of safety valve 204 that include air flow rates in a closed position.

In addition, similar to exhale valve 202, safety valve 204 may be a removable element to allow replacement with another safety valve 204 or alternative component. Safety valve 204 may be removable based upon any type of sealed connection. For example, safety valve 204 may be connected to mask 200 by a threaded connection, a friction connection, a pressure connection, an adhesive connection or any other connection or combination of connections. A replaceable safety valve 204 may be beneficial for improving sanitary conditions of the mask and/or operation for the user.

Mask 200 also includes access port 206 with access port seal 208. Access port 206 allows access to provide a user with liquids, medicines, and other items. Access port seal 208 provides a flexible seal that allows straws, syringes, medicine droppers, thermometers, patient monitoring devices, and other supplies to pass through while minimizing loss of conditioned air from mask 200. In some embodiments, access port seal 208 is a replaceable wafer designed to fit access port 206 and remain in place during use of access port 206. The replaceable wafer may be periodically replaced to increase sanitary conditions during use of mask 200 or to allow alternative operations. One skilled in the art will recognize that the shape and design of access port 206 and access port seal 208 may vary and remain within the scope and spirit of the present disclosure. Access port seal 208 may be constructed of any flexible and sealable material, such as silicone or PVC materials. In addition, access port seal 208 may include slits in a crossed or other shaped pattern to allow insertion of supplies.

Access port 206 may also be used to connect additional medical systems and or apparatus. For example, a nebulizer system output may be fitted to a connector that may be attachable to access port 206. In such an example, access port seal 208 may be unaltered, removed, or replaced with an alternative access port seal 208 designed for the selected operation. The nebulizer system output connector may be connected to access port 206 by a threaded connection, a friction connection, a pressure connection, an adhesive connection or any other connection or combination of connections. In such a system nebulized liquid may be provided to the user through access port 206.

FIG. 4 depicts three rings on the side of mask 200 that engage a user's face during operation. As discussed herein, the rings will be referred to as molding ring 210, skin sensor ring 212, and contact ring 214. One skilled in the art will recognize that three rings are depicted for illustrative purposes and the functions and layering of the rings may vary and remain within the scope and spirit of the disclosure. For example, the rings may be combined in one or more rings, or integrated into the edge of mask 200.

Molding ring 210 is comprised of a moldable material that is flexible, but will maintain its shape after molding. For example, aluminum. Molding ring 210 may be molded to fit a user's facial structure in order to improve the contact between the user and mask 200.

Skin sensor ring 212 is used to detect contact with a user's skin. Skin sensor ring 212 may trigger a warning that mask 200 is not in contact with the skin and should be checked. In addition, skin sensor ring 212 may trigger the O2 delivery system to stop providing oxygen until mask 200 is returned to an operational position. Skin sensor ring 212 may comprise a capacitive sensor layer, whereby skin sensor ring 212 has one capacitance when in contact with the user's skin, and said capacitance will change when the pressure against said user's face changes. For example, the capacitance will change when mask 200 is removed from the user's face, and skin sensor 212 will indicate the change in pressure in the contact sensor.

Contact ring 214 provides direct contact with a user's skin and is designed to minimize friction movement between a person's skin and the mask in order to limit skin damage caused by mask 200. Contact ring 214 may include a nonslip material such as neoprene for contact with the skin.

The inside of mask 200 may include one or more sanitary sheets formed to match the internal walls of mask 200 without interfering with the operation of exhale valve 202, safety valve 204, access port 206, access port seal 208, or mask rings 210-214. Sanitary sheets may be in removable contact with the internal walls of mask 200 or additional sanitary sheets. During use, the sanitary sheets may be periodically removed from the inside of mask 200 to expose a clean surface for ongoing operation of mask 200, increasing sanitary conditions for use of mask 200. Utilizing the removable sanitary sheets minimizes the time that a user is without conditioned air delivery when the mask is removed for cleaning purposes.

In this embodiment, input port 216 is attached to the bottom of mask 200. The placement of input port 216 may vary and remain within the scope and spirit of the present disclosure. Input port 216 is designed to allow slower velocity airflow into mask 200. The shape and/or material of input port 216 may be varied to help dampen the sound of airflow in the air delivery system. For example, input port 216 may be made of a material that will dampen (or filter) the frequencies of the air noise without inhibiting the frequencies a user's voice.

Attached to input port 216 is input port tubing 218 which provides conditioned air to the user. In some embodiments, input port tubing 218 is flexible but collapse resistant, and includes airflow noise reducing characteristics. These characteristics may be incorporated by the type of material and/or design of the tubing used for input port tubing 218. In other embodiments, input port tubing 218 is stock tubing that may be used with a variety of medical equipment. In some embodiments, the length of input port tubing 218 is designed to help move other components away from mask 200. The distance may reduce noise around mask 200 caused by other components. One skilled in the art will recognize that a variety of tubing may be employed for input port tubing 218 and remain within the scope and spirit of the present disclosure.

In this embodiment, at the opposite end of input port tubing 218 is output coupling 220. Output coupling 220 connects input port 216 to the flow rate throttling valve 222 through input port tubing 218, and also connects the air reservoir 226 via reservoir tube 224. Output coupling 220 includes a flow director that forces air to flow into the air reservoir 226. The air may then come out of the air reservoir 226 and up to mask 200. In some embodiments, output coupling 220 may be located in alternative locations in the air delivery system depending upon locations of other components. For example, output coupling may be connected directly to input port 216.

In this embodiment, flow rate throttling valve 222 is connected to output coupling 220 and air modification module 230. Flow rate throttling valve 222 may be located in a variety of locations in the oxygen delivery system, such as at or near the O2 source or attached to mask 200. One skilled in the art will recognize that characteristics of various embodiments of flow rate throttling valve 222, such as weight, may affect placement in the oxygen delivery system. For example, an embodiment of flow rate throttling valve 222 that is heavy may increase the chances of skin damage if attached to mask 200 than a lighter embodiment of flow rate throttling valve 222.

In this embodiment, flow rate throttling valve 222 controls the input of air into output coupling 220. Flow rate throttling valve 222 may conserve oxygen use by controlling the supply of oxygen to when oxygen is needed and minimizing the flow of oxygen when it is not needed. Flow rate throttling valve 222 also regulates the output pressure to be as close to 0 psi as possible while still positive, thus preventing a negative pressure on the output side of flow rate throttling valve 222. In some embodiments, flow rate throttling valve 222 also acts as a backflow preventer or check valve insuring that exhaled air is exhausted through exhale valve 202 or safety valve 204 in mask 200. In some embodiments, flow rate throttling valve 222 is mechanical. In other embodiments, flow rate throttling valve 222 is electronic.

In some embodiments, flow rate throttling valve 222 will include an indicator showing a rate of flow. The indicator may not be a gauge for accurate measurement, but will show that flow rate throttling valve 222 is functioning and/or the patient is breathing on their own. In some embodiments, the indicator will be electronic. In some embodiments, the indicator may be associated with an airflow sensor. The airflow sensor may operate as an electronic or mechanical sensor or plurality of sensors in the air delivery system. For example, the airflow sensor may include a diaphragm that oscillates with the airflow in the system, and presses against a translucent material whereby a user or other person can observe the airflow oscillation by monitoring the movement of the diaphragm. The pattern may be visually enhanced by using a polarized material for the diaphragm and translucent material, such that the diaphragm is easily seen when in a state next to the translucent material and is not apparent when separated from the translucent material.

In some embodiments, flow rate throttling valve 222 may include a control interface to allow a person to set or adjust the output of flow rate throttling valve 222. The control interface may be mechanical or electronic, including programmed adjustments that may be applied based upon sensors in the oxygen delivery system. The control interface may be adjustable by a user, a caregiver, technician, or other person. In some embodiments, the control interface may only be operated by authorized personnel. For example, the control interface may be password protected. For another example, the control interface may be a removable knob that is kept by the authorized personnel.

The oxygen delivery system includes air reservoir 226 which may be a reserve capacity bag or flexible container designed to hold air. In this embodiment, air reservoir 226 is connected by reservoir tube 224 to output coupling 220. In some embodiments, air reservoir 226 may be connected by reservoir tube 224 to either the input side or the output side of flow rate throttling valve 222.

During operation of the oxygen delivery system, air reservoir 226 contains a reserve supply of oxygen rich air. Air reservoir 226 may be filled from oxygen rich air directed from flow rate throttling valve 222 by output coupling 220. A user may utilize the reserve O2 supply in air reservoir 226 as needed. In some embodiments, air reservoir 226 is flexible and as flat as possible to prevent it from "getting in the way" of the user. In addition, air reservoir 226 is designed to insure that if the patient oxygen volume requirements exceed the maximum available, air reservoir 226 does not create a negative pressure on the output side of flow rate throttling valve 222.

In some embodiments, air reservoir 226 will also provide the caregiver or user the ability to force the reserve air into the patient's lungs at a higher pressure than normal by simply squeezing air reservoir 226. For example, upon feeling the initial effects of low oxygen in the system, a user may apply pressure to air reservoir 226 in order to increase the oxygen intake and minimize harm from reduced oxygen in the body. In such embodiments, air reservoir 226 must also be strong enough to withstand being squeezed to provide life sustaining positive pressure on the output port (or into the mask). For example, air reservoir 226 may be used as a ventilator bag and/or to reduce the burden on the patient in drawing a breath.

In the embodiment shown, air reservoir 226 is an ellipsoid shape with expandable folds. The shape of air reservoir 226 may vary and remain within the scope and spirit of the present disclosure. For example, air reservoir 226 may be designed as a banana shape. In some embodiments, air reservoir 226 may be placed under the oxygen delivery system user's arm to allow users with insufficient hand strength to squeeze air reservoir 226 with their arm. The placement of air reservoir 226 for the user is dependent on the embodiment of air reservoir 226 used and the user's abilities and preferences.

In the embodiment shown, air reservoir 226 is shown as a two liter reservoir, but one skilled in the art will recognize that the volume of air reservoir 226 may vary. For example, air reservoir 226 may hold one liter of oxygen by volume. For another example, air reservoir 226 may hold enough oxygen by volume for a person to take two natural breaths.

In some embodiments, reservoir tube 224 is flexible but collapse resistant, and includes airflow noise reducing characteristics. These characteristics may be incorporated by the type of material and/or design of the tubing used for reservoir tube 224. Reservoir tube 224 may be a large diameter tubing to allow low pressure air flow. In other embodiments, reservoir tube 224 is stock tubing that may be used with a variety of medical equipment. One skilled in the art will recognize that a variety of tubing may be employed for reservoir tube 224 and remain within the scope and spirit of the present disclosure.

In some embodiments, the oxygen delivery system may include an alarm or warning system. The alarm or warning system may be associated with one or more components of the oxygen delivery system. In some embodiments, an alarm or warning system component may be attached to output coupling 220 and may be triggered based upon airflow characteristics from reservoir tube 224. For example, if a threshold airflow is surpassed from reservoir tube 224, a warning is provided for a caretaker to check with the user regarding the use of air reservoir 226. Such a system may use one or more airflow sensors to monitor at least one of an air pressure, a flow rate of the air, an air temperature, and/or the air content. In some embodiments, an alarm or warning system component may be triggered manually by a user. For example, the user may press a button in order to provide an alarm to get the attention of the caregiver. In some embodiments, the alarm or warning system may provide an alarm to a caregiver if a malfunction in the oxygen supply system is detected.

In this embodiment, air modification module 230 mixes the oxygen supply with either water vapor or medicine to prevent drying out the nasal passages and mouth of the patient. Air modification module 230 is located at the input to flow rate throttling valve 222. In this embodiment, the O2 source (not shown) is connected to the input for air modification module 230 via O2 input tube 228. The O2 source may be any type of oxygen source, such as an O2 tank or regulator. One skilled in the art will recognize that the location of air modification module 230 may vary and remain within the scope and spirit of the present disclosure. For example, air modification module 230 may be located at the output to output coupling 220 or at mask 200.

In some embodiments, air modification module 230 is designed to hold replaceable cartridges containing a moisture component. The moisture component may be water, saline, medicines, or other liquids that may be aerosolized. In some embodiments, cartridges may contain a sponge or similar material that entrains and/or holds liquids and allows air to pass through, whereby the air pulls aerosolized particles of the liquid from the material to continue with the airflow. One skilled in the art will recognize that air pressures may be modified to account for the resistance to airflow caused by the sponge-like material and maintain positive pressure in the system. In some embodiments of the cartridge, the sponge-like material may be in contact with a liquid reservoir, whereby the sponge-like material entrains the liquid during operation.

In addition, one skilled in the art will recognize that the shape, size, and design of the cartridges may vary and remain within the scope and spirit of the present disclosure. For example, the cartridge may include a sponge-like material in the shape of a hollow cylinder with a sealed surface on one end and open on the other. During operation the sealed surface is directed to the airflow input of air modification module 230 and directs air to the exterior wall of the cylindrical sponge-like material. Air will flow through the sponge-like material to the center of the hollow cylindrical shape aerosolizing the contained liquid and leaving the output of air modification module 230. For another example, the cartridge may include a sponge-like material in the shape of a box with numerous fins to increase surface area, similar to an air filter.

During operation the airflow input of air modification module 230 directs air to one side of the sponge-like material. Air will flow through the sponge-like material to the opposite side aerosolizing the contained liquid and leaving the output of Air modification module 230.

In some embodiments, cartridges may include components to inject aerosolized particles of liquid into an airstream. The injection of particles may be controlled in a variety of manners, such as timing systems, manual controls, mechanical controls, electric controls, or some combination of controls. For example, injection may be controlled by a breath detection system such as an airflow sensor.

In some embodiments, the oxygen delivery system may include a liquid recapture system (not shown) to collect lost fluids, such as medicines, from inside mask 200 and direct the recaptured fluids to air modification module 230.

FIG. 5 shows an embodiment of an air delivery system of the disclosure. Similar to FIG. 4, mask 300 is designed to fit a user's face, covering the nose and mouth of a user, and allows a user to breathe normally while providing conditioned air content. In some embodiments, the edge of mask 300 in contact with a user may be designed for a variety of purposes as described elsewhere herein. In this embodiment, mask 300 includes exhale valve 302, safety valve 304, and access port 306.

Exhale valve 302 and safety valve 304 may be designed and utilized as described elsewhere herein. Generally, exhale valve 302 provides a means for exhaled gas to exit mask 300, and safety valve 304 may operate to remove exhaled gas from mask 300 and/or improve the efficiency of the delivery of conditioned air content to a user.

Mask 300 also includes access port 306 which is designed to operatively engage access port seals 308. Access port 306 allows access to provide a user with liquids, medicines, alternative airflow, and other items. Access port seals 308 provide a seals that allows straws, syringes, medicine droppers, thermometers, patient monitoring devices, and other supplies to pass through while minimizing loss of conditioned air from mask 300, and/or allow the connection of mask 300 to other medical systems. In this embodiment, the access port seals 308 shown include replaceable seals with (1) slits in a crossed or other shaped pattern to allow insertion of supplies, or (2) a tube connector. One skilled in the art will recognize that the design and operation of access port seals 308 may vary and remain within the scope and spirit of the present disclosure.

Each access port seal 308 is designed to fit access port 306 and remain in place during use of access port 306. For example, the replaceable seal with slits may slide into access port 306 from one direction and remain in place with a fitted connection. For another example, the tube connection seal may be designed with a keyed system wherein the tube connection is placed into access port 306 such that extensions on the seal match cut outs in access port 306, and by turning the tube connection seal, protrusions on said seal engage a fitted connection with access port 306. Fitted connections may be based upon a set of paired protrusions and/or indentions found on access port seals 308 and access port 306, wherein paired protrusions and/or indentions of the access port seals 308 engage the corresponding elements in access port 306 when the access port seals 308 are placed in operative position with access port 306. One skilled in the art will recognize that design and method for operatively attaching access port seals 308 with access port 306 may vary and remain within the scope and spirit of the present disclosure.

FIG. 5 also depicts a harness for holding mask 300 in place while engaged with a user's face during operation. An expanded view of the harness and mask 300 is provided in FIG. 6 and elements identified in FIG. 6 may be referred to herein. In this embodiment, the harness comprises adjustable straps with ear pieces 310 and headpiece 314. Headpiece 314 is designed to distribute the pressure of holding mask 300 in place across a wide area of the user's head in order to minimize potential skin damage or headaches that may occur due to localized pressure points. Pressure on mask 300 may be created through elasticity in headpiece 314, ear pieces 310, adjustable straps, and/or strap attachments 338. Pressure is directed to insure a tight seal on a user's face during operation. For example, the design and placement of head piece 314 may create a slight upward pressure on the bottom of mask 300 to create a tight seal along the bottom of mask 300.

In this embodiment, headpiece 314 is shown as one solid material. In other embodiments, headpiece 314 may be designed with a variety of holes or other gaps that maintain a distributed pressure and alter the comfort, elasticity, or other attributes of headpiece 314. In some embodiments, headpiece 314 may be made of an elastic material, such as neoprene, with protrusions to limit the contact with the head while maintaining a pressure distribution. One skilled in the art will recognize that the design, material, and placement of headpiece 314 may vary and remain within the scope and spirit of the disclosure. For example, the thickness, shape, size, material, and cutouts of headpiece 314 may be altered among embodiments to create alternatives to customize the distribution of pressure on the head while maintaining a seal at mask 300.

The adjustable straps shown in this embodiment include ear pieces 310 and adjustment protrusions 312. Ear pieces 310 are curved to fit over the ears to prevent contact with a user's ear in order to minimize irritation to the user and/or damage to the user's skin. Ear pieces 310 are designed to transfer forces necessary to hold mask 300 in place around a user's ear. In order to transfer forces applied to the adjustable straps around the user's ear, ear pieces 310 may be made of rigid or semi-rigid materials. In some embodiments, the material for ear pieces 310 may be sufficiently rigid to transfer forces necessary to maintain the seal at mask 300, but moldable to customize the shape for a user's comfort.

The placement of ear pieces 310 may be customized for a user by adjusting the position of ear pieces 310 from mask 300 and headpiece 314. In this embodiment, mask 300 and headpiece 314 each have strap attachments 338 wherein the ends of adjustable straps slide through and are held in place by friction created by adjustment protrusions 312. The placement of strap attachments 338 in relation to adjustment protrusions 312 set the position of the components of the harness. One skilled in the art will recognize that the design of any adjustment system may vary and remain within the scope and spirit of the present disclosure. In addition, one skilled in the art will recognize that some embodiments may have a fixed placement for the harness and not allow adjustment of the elements.

In some embodiments, adjustable straps and strap attachments 338 may be designed to minimize friction with a user's skin or hair and therefore minimize the risk of irritation or chafing to the user. For example, adjustable straps and strap attachments 338 may be made of material that limits friction with skin. In another example, strap attachments may include protrusions to minimize chafing a user's skin, such as raised rails 340.

In this embodiment, input port 316 is attached to the bottom of mask 300. As described above, input port 316 is designed to allow slower velocity airflow into mask 300, and may help dampen the sound of airflow in the air delivery system.

Attached to input port 316 in this embodiment is air modification module 332. An embodiment of air modification module 332 is shown with expanded components in FIG. 5 and with further detail in FIG. 7. One design for connecting air modification module 332 to input port 316 is shown in FIG. 7. In this embodiment, output 356 of air modification module 332 includes two extensions 358 which correspond to a pair of "L" shaped grooves 360 located in the interior wall of input port 316. Seal 362 is placed on output 356 of air modification module 332, which is inserted into input port 316 wherein the extensions 358 slide in grooves 360 and air modification module 332 is turned to lock the extensions 358 into the "L" shaped grooves 360. One skilled in the art will recognize that connections between any elements of the air delivery system may include a similar connection to that described between air modification module 332 and input port 316. In addition, one skilled in the art will recognize that the design and operation for connecting elements of the air delivery system may vary and remain within the scope and spirit of the disclosure. For example, elements may be connected by a threaded connection, a friction connection, a pressure connection, an adhesive connection or any other connection or combination of connections.

One skilled in the art will recognize that air modification module 332 may be designed and operated as described elsewhere herein. Generally, air modification module 332 mixes the oxygenated air supply with additives such as water vapor or medicine for the user to breathe. In some embodiments, the additives may help prevent drying out the nasal passages and mouth of the patient. One skilled in the art will recognize that the location of air modification module 332 may vary and remain within the scope and spirit of the present disclosure.

In the depicted embodiment, air modification module 332 is designed to hold replaceable cartridges 336 containing air modification components. In the depicted embodiment, one of the replaceable cartridges 336 is placed within the cavity of air modification module 332 and removable cap 334 is placed over the side opening of air modification module 332 creating an airtight or nearly airtight seal. One skilled in the art will recognize that the air delivery system may operate without a replaceable cartridge 336 in air modification module 332 whereby the oxygenated air from input tube 318 will pass through air modification module 332 unchanged to mask 300. Alternatively, in some embodiments of an air delivery system, the air modification module 332 may not be included.

Each of replaceable cartridges 336 fit within air modification module 332 such that an airtight seal is created at output 356. The fit of each replaceable cartridge 336 with air modification module 332 is designed to direct airflow from the input of air modification module 332 through each replaceable cartridge 336 such that at least one air modification component (such as a saline or medicine as described elsewhere herein) is aerosolized into the airflow that exits through output 356. As further described herein and as will be understood by one skilled in the art, the affect on airflow for each replaceable cartridge 336 may vary and remain within the scope and spirit of the disclosure.

An expanded view of air modification module 332 in FIG. 7 provides additional detail of the air modification module 332 and the replaceable cartridges 336. FIG. 7 depicts hollow cylindrical cartridge 342, jet injection cartridge 348, and folded cartridge 352 as representative replaceable cartridges 336.

In this embodiment, hollow cylindrical cartridge 342 includes a sponge-like material in the shape of a hollow cylinder. In this embodiment, hollow cylinder interior wall 344 includes numerous fins to increase the surface area of hollow cylinder interior wall 344. Hollow cylindrical cartridge 342 also includes a sealed surface on the airflow input end and opening on the airflow output end. At least one foot 346 on hollow cylindrical cartridge 342 raises the sealed surface from the input side of air modification module 332 allowing airflow around the sealed surface. During operation the sealed surface directs air to the exterior wall of the cylindrical sponge-like material. Air will flow through the sponge-like material to the center of the hollow cylindrical shape aerosolizing the contained liquid and leaving output 356 of air modification module 332.

Jet injection cartridge 348 is a cylindrical cartridge with an airflow pathway directly through the cartridge, and includes injection nozzles 350 that dispense particles of liquid and/or solids into the airstream. The injection of particles may be controlled in a variety of manners, such as timing systems, manual controls, mechanical controls, electric controls, or some combination of controls. For example, injection may be controlled by a breath detection system or another sensor system.

Folded cartridge 352 is a cylindrical cartridge that includes a sponge-like material in the cylinder with numerous fins on the cartridge output surface 354 to increase surface area, similar to an air filter. During operation, the airflow input of air modification module 332 directs air to one side of the sponge-like material. Air will flow through the sponge-like material to the output surface 354 aerosolizing the contained liquid and leaving output 356 of air modification module 332. One skilled in the art will recognize that the shape, size, and design of replaceable cartridges 336 may vary and remain within the scope and spirit of the present disclosure.

In some embodiments, replaceable cartridges 336 may contain a liquid air modification component such as water, saline, medicines, or other liquids that may be aerosolized. In some embodiments containing a moisture component, cartridges may contain a sponge or similar material that entrains and/or holds liquids and allows air to pass through, whereby the air pulls aerosolized particles of the liquid from the material to continue with the airflow. One skilled in the art will recognize that air pressures may be modified to account for the resistance to airflow caused by the sponge-like material and maintain positive pressure in the system. In some embodiments of the cartridge, the sponge-like material may be in contact with a liquid reservoir, whereby the sponge-like material entrains the liquid during operation.

Some replaceable cartridges 336 may contain a solid air modification component such as a medicine. The medicine may be in a powdered format for dispersal or may be pulverized by the cartridge or air modification module 332 into a usable powder. One skilled in the art will recognize that designs to facilitate aerosolizing solid particulate into the air for disbursement to the user may vary and remain within the scope and spirit of the disclosure.

Attached to the input of air modification module 332 in this embodiment is input tubing 318 which provides oxygenated air to air modification module 332. Input tubing 318 may be flexible but collapse resistant, and includes airflow noise reducing characteristics. Input tubing 318 may include the characteristics and design of tubing discussed elsewhere herein.

In this embodiment, at the opposite end of input tubing 318 is output coupling 320 which connects air modification module 332 to flow rate throttling valve 322 through input tubing 318, and connects the air reservoir 326 via reservoir tube 324. As discussed with other embodiments herein, output coupling 320 includes a flow director that forces conditioned air to flow into the air reservoir 326. The reserve air may then come out of the air reservoir 326 and up to mask 300.

In this embodiment, flow rate throttling valve 322 is connected to output coupling 320 and air input port 330. The characteristics, design, and operation of flow rate throttling valve 322 are described further with regard to other embodiments described herein. As described more fully elsewhere herein, flow rate throttling valve 322 controls the input of air into output coupling 320.

The oxygen delivery system includes air reservoir 326 which may be a reserve capacity bag or flexible container designed to hold air. In this embodiment, air reservoir 326 is connected by reservoir tube 324 to output coupling 320. Air reservoir 326 operates as a reserve supply of oxygen rich air which may be used as needed by the user. Air reservoir 326 may be designed, operated, and utilized as described in more detail elsewhere herein. In addition, reservoir tube 324 may include characteristics and designs of other tubing discussed in more detail elsewhere herein.

In the depicted embodiment, air reservoir 326 is flexible bag with an elongated ellipsoid shape having a curve. In some embodiments, air reservoir 326 may be placed under the air delivery system user's arm to allow users with insufficient hand strength to squeeze air reservoir 326 with their arm.

FIG. 8 shows an embodiment of an oxygen delivery system of the disclosure. Similar to other embodiments described herein, mask 400 is designed to fit a user's face, covering the nose and mouth of a user, and allows a user to breathe normally while providing conditioned air content. In this embodiment, mask 400 includes exhale valve 402, safety valve 404, access port 406, and contact rings 410.

Exhale valve 402 and safety valve 404 may be designed and utilized as described above. Exhale valve 402 provides a means for exhaled gas to exit mask 400, and safety valve 404 may operate to remove exhaled gas from mask 400 and/or improve the efficiency of the delivery of conditioned air content to a user.

Mask 400 also includes access port 406 which allows access to provide a user with liquids, medicines, alternative airflow, and other items. In this embodiment, access port 406 is depicted with a tube connection interface. In addition, alternative access port seal 408 is shown that may replace the tube connection interface in access port 406. Alternative access port seal 408 provides a seal that allows straws, syringes, medicine droppers, thermometers, patient monitoring devices, and other supplies to pass through while minimizing loss of conditioned air from mask 400. The design, characteristics, and operation of access ports and access port seals are described further elsewhere herein.

Contact rings 410 depicted in FIG. 8 represent elements that may be attached to or part of the edge of mask 400 that engages a user's face during operation. Contact rings 410 may include one or more of a molding element, a skin sensor element, and a skin protection element. These elements are described in more detail with respect to other embodiments herein, including the molding ring, skin sensor ring, and contact ring described with respect to FIG. 4. One skilled in the art will recognize that three rings are depicted for illustrative purposes and the functions and layering of the rings may vary and remain within the scope and spirit of the disclosure.

FIG. 8 also depicts a harness for holding mask 400 in place while engaged with a user's face during operation. In this embodiment, the harness comprises a headpiece 412 with mask connection straps, and an overhead strap 414. Headpiece 412 is designed to distribute the pressure of holding mask 400 in place across a wide area of the user's head.

Pressure on mask 400 may be created through elasticity in headpiece 412 and/or overhead strap 414. Pressure is directed to insure a tight seal on a user's face during operation. For example, the design and placement of head piece 412 and overhead strap 414 may create a slight upward pressure on the bottom of mask 400 to create a tight seal along the bottom of mask 400.

In this embodiment, headpiece 412 is shown as a curved ellipsoid with a variety of holes. The holes may provide additional flexibility to the material selected, and may increase a user's comfort. For example, the holes may provide better airflow to the user's head. Headpiece 412 may be made of an elastic material, such as neoprene, with protrusions to limit the contact with the head while maintaining a pressure distribution. One skilled in the art will recognize that the design, material, and placement of headpiece 412 may vary and remain within the scope and spirit of the disclosure. For example, the thickness, shape, size, material, and cutouts of headpiece 412 may be altered among embodiments to create alternatives to customize the distribution of pressure on the head while maintaining a seal at mask 400.

Extending from headpiece 412 are mask connection straps that create an angle to separate connection points on the mask. The meeting point of the angle may be designed to be above a user's ear to minimize discomfort and/or skin damage to the ear. In addition, overhead strap 414 is located near the meeting point of mask connection straps and during operation, extends across the top of a user's head. In some embodiments, the connection of overhead strap 414 to headpiece 412 may allow adjustments to customize the position of overhead strap 414 for the user. For example, in the depicted embodiment, the loops at the end of overhead strap 414 may slide forward and backward along headpiece 412. In other embodiments, overhead strap 414 may be fixed to a specific location on headpiece 412. The connection straps may be adjusted in connection with mask 400 to further alter the comfort and seal of mask 400 on the user's face. In some embodiments, any excess length of connection straps may be cut off once a preferred engagement of mask 400 is determined for the user.

The length of overhead strap 414 may be adjusted to provide lift at the point of connection with headpiece 412 without creating excessive pressure across the top of a user's head which may cause skin damage or headaches. In the depicted embodiment, overhead strap 414 is two pieces that are adjustably attached over the top of a user's head with, for example, hook and loop tape. One skilled in the art will recognize that the type of adjustable attachment may vary and remain within the scope and spirit of the disclosure. In some embodiments, overhead strap 414 is designed to lift headpiece 412 above a user's ear in order to prevent potential discomfort or damage to the user's ear and skin.

In this embodiment, input port 416 is attached to the bottom of mask 400. As described above, input port 416 may be designed to allow slower velocity airflow into mask 400, and may help dampen the sound of airflow in the air delivery system.

Attached to input port 416 in this embodiment is air modification module 432. One skilled in the art will recognize that air modification module 432 and parts thereof may be designed and operated as described elsewhere herein. Air modification module 432 may mix the conditioned air supply with additives such as water vapor or medicine for the user to breathe. One skilled in the art will recognize that the location of air modification module 432 may vary and remain within the scope and spirit of the present disclosure.

Attached to the input of air modification module 432 in this embodiment is input tubing 418 which provides oxygenated air to air modification module 432. Input tubing 418 may be flexible but collapse resistant, and includes airflow noise reducing characteristics. Input tubing 418 may include the characteristics and design of tubing discussed elsewhere herein.

At the opposite end of input tubing 418 is output coupling 420 which connects air modification module 432 to flow rate throttling valve 422 through input tubing 418, and connects the air reservoir 426 via reservoir tube 424. Output coupling 420 may be designed and operate as provided elsewhere herein.

In this embodiment, flow rate throttling valve 422 is connected to output coupling 420 and air input port 430 which receives conditioned air through air input tube 428. The characteristics, design, and operation of flow rate throttling valve 422 are described further with regard to other embodiments described herein. As described more fully elsewhere herein, flow rate throttling valve 422 controls the input of air into output coupling 420.

Air reservoir 426 operates as a reserve supply of oxygen rich air which may be used as needed by the user. Air reservoir 426 may be designed, operated, and utilized as described in more detail elsewhere herein. In addition, reservoir tube 424 may include characteristics and designs of other tubing discussed in more detail elsewhere herein.

In the depicted embodiment, air reservoir 426 is flexible bag with an elongated cylindrical shape having folds designed for compression along the length of the cylindrical shape. In some embodiments, air reservoir 426 may be attached to a surface whereby a user of the oxygen delivery system or a caregiver may compress air reservoir 426 by pressing one end of air reservoir 426 towards the opposite end of air reservoir 426 which is attached to a surface. In some embodiments, the surface may be part of a wheelchair, bed, or other item that is in regular association with the user.

Air reservoir 426 may be attached to the surface in a fixed or removable manner. In some embodiment, a removable air reservoir 426 and/or reservoir tube 424 may be associated with a sealable disconnect to allow the user mobility. For example, a user may have one air reservoir 426 attached to their bed and one air reservoir 426 attached to their wheelchair. The user may choose to disconnect the reservoir tube 424 from the reservoir on the bed and attach it to the reservoir on the wheelchair to provide more mobility during the day. Reservoir tube 424 may include a seal such that when it is disconnected, reservoir tube 424 is sealed to maintain the fluidity of airflow to mask 400 during the transition, and is reopened when reconnected to an air reservoir 426.

FIG. 9 shows an embodiment of an air delivery system of the disclosure. Similar to other embodiments described herein, mask 500 is designed to fit a user's face, covering the nose and mouth of a user, and allows a user to breathe normally while providing conditioned air content. Mask 500 may be designed and operated as described further with regard to other embodiments disclosed herein. In this embodiment, mask 500 includes exhale valve 502, and safety valve 504.

Exhale valve 502 and safety valve 504 may be designed and utilized as described above. Exhale valve 502 provides a means for exhaled gas to exit mask 500, and safety valve 404 may operate to remove exhaled gas from mask 500 and/or improve the efficiency of the delivery of conditioned air content to a user.

In this embodiment, mask 500 does not include an access port. Accordingly, mask 500, input port 516, and/or input tubing 518 may be removed temporarily to allow access and provide a user with liquids, medicines, alternative airflow, and other items as necessary. One skilled in the art will recognize that an access port as described elsewhere herein may be included in mask 500.

In this embodiment, input port 516 is attached to the front of mask 500. As described above, input port 516 may be designed to allow slower velocity airflow into mask 500, and may help dampen the sound of airflow in the air delivery system. One skilled in the art will recognize that the orientation of input port 516 on mask 500 may vary and remain within the scope and spirit of the disclosure.

Attached to input port 516 in this embodiment is input tubing 518 which provides conditioned air to mask 500 through input port 516. Input tubing 518 may be flexible but collapse resistant, and includes airflow noise reducing characteristics. Input tubing 518 may include the characteristics and design of tubing discussed elsewhere herein.

At the opposite end of input tubing 518 is air modification module 532. One skilled in the art will recognize that air modification module 532 and parts thereof may be designed and operated as described elsewhere herein. Air modification module 532 may mix the conditioned air supply with additives such as water vapor or medicine for the user to breathe. One skilled in the art will recognize that the location of air modification module 432 may vary and remain within the scope and spirit of the present disclosure.

Attached to the input of air modification module 532 in this embodiment is output coupling 520 which connects air modification module 532 to flow rate throttling valve 522 and air reservoir 526 via reservoir tube 524. Output coupling 520 may be designed and operate as provided elsewhere herein.

In this embodiment, flow rate throttling valve 522 is connected to output coupling 520 and air input port 530 which receives conditioned air through air input tube 528. The characteristics, design, and operation of flow rate throttling valve 522 are described further with regard to other embodiments described herein. As described more fully elsewhere herein, flow rate throttling valve 522 controls the input of conditioned air into output coupling 520.

Air reservoir 526 operates as a reserve supply of oxygen rich air which may be used as needed by the user. In the depicted embodiment, air reservoir 526 is flexible bag with an elongated ellipsoid shape having a curve. One skilled in the art will recognize that air reservoir 526 may be designed, operated, and utilized as described in more detail elsewhere herein. In addition, reservoir tube 524 may include characteristics and designs of other tubing discussed in more detail elsewhere herein.

FIG. 10 shows an embodiment of a mask 600 and harness 602 of an oxygen delivery system of the disclosure. Similar to other embodiments described herein, mask 600 is designed to fit a user's face, covering the nose and mouth of a user, and allows a user to breathe normally while providing conditioned air content. Mask 600 may be designed and operated as described further with regard to other embodiments disclosed herein. One skilled in the art will recognize that additional elements described elsewhere herein may be included in mask 600.

Safety valve 604 may be designed and utilized as described above. Safety valve 604 may operate to remove exhaled gas from mask 600 and/or improve the efficiency of the delivery of conditioned air content to a user.

Mask 600 also includes access port 606 which is designed to operatively engage access port seals 608 and 610, wherein one of access port seals 608 and 610 may be engaged during operation. One skilled in the art will recognize that some embodiments of access port 606 may engage a plurality of access port seals 608 and/or 610 simultaneously and remain within the scope and spirit of the disclosure. Access port 606 allows access to provide a user with liquids, medicines, alternative airflow, and other items. Access port seals 608 and 610 provide a seal that allows straws, syringes, medicine droppers, thermometers, patient monitoring devices, and other supplies to pass through while minimizing loss of conditioned air from mask 600, and/or allow the connection of mask 600 to other medical systems. In this embodiment, the access port seal 608 is shown with slits in a crossed or other shaped pattern to allow insertion of supplies, and access port seal 610 is shown as a tube connector. One skilled in the art will recognize that the design and operation of access port seals may vary and remain within the scope and spirit of the present disclosure.

Access port seals 608 and 610 are designed to fit access port 606 and remain in place during use of access port 606. For example, access port seal 608 may slide into access port 606 from seal entry 612 and remain in place with a fitted connection. For another example, access port 610 may be designed with a keyed system wherein access port seal includes extensions that match keyed cutouts 614 in access port 606. When access port seal 610 is placed into access port 606, such that extensions on the seal pass through keyed cutouts 614, and is turned, protrusions on access port seal 610 engage a fitted connection with access port 606. One skilled in the art will recognize that design and method for operatively attaching access port seals 608 with access port 606 may vary and remain within the scope and spirit of the present disclosure. The design, characteristics, and operation of access ports and access port seals are described further elsewhere herein.

In this embodiment, input port 616 is attached to the bottom of mask 600. As described above, input port 616 may be designed to allow slower velocity airflow into mask 600, and may help dampen the sound of airflow in the conditioned air delivery system.

FIG. 10 also depicts harness 602 for holding mask 600 in place while engaged with a user's face during operation. In this embodiment, the harness comprises a headpiece and a pair of overhead straps 624 and 626. The headpiece is made up of a pair of side straps 618 and 620 which are separated by strap separator 622. The head piece is designed to distribute the pressure of holding mask 600 in place across a wide area of the user's head. Pressure on mask 600 may be created through elasticity in side straps 618 and 620 and/or overhead straps 624 and 626. Pressure is directed to insure a tight seal on a user's face during operation. For example, the design and placement of the straps may create a slight upward pressure on the bottom of mask 600 to create a tight seal along the bottom of mask 600.

In this embodiment, side strap 618 attaches to the lower part of mask 600 and curves around the upper part of the back of a user's head and side strap 620 attaches to the upper part of mask 600 and curves around the lower part of the back of a user's head. Strap separator 622 is designed to maintain a separation of side straps 618 and 620 at the back of a user's head. Strap separator 622 may be made with a rigid or semi-rigid material in order to prevent side straps 618 and 620 from collapsing upon each other. Strap separator 622 may be made of a flat and soft material to minimize discomfort to a user that may rest against the back of their head. Strap separator 622 may be fixed to or adjustable with side straps 618 and 620. In some embodiments, a plurality of strap separators 622 may be used between side straps 618 and 620.

Side straps 618 and 620 may be made of an elastic material, such as neoprene, with protrusions to limit the contact with the head while maintaining a pressure distribution. One skilled in the art will recognize that the design, material, and placement of side straps 618 and 620 may vary and remain within the scope and spirit of the disclosure. For example, the thickness, shape, size, material, and cutouts of side straps 618 and 620 may be altered among embodiments to create alternatives to customize the distribution of pressure on the head while maintaining a seal at mask 600. In some embodiments, the location where side straps 618 and 620 cross is designed to be at or around the location of a user's ear in order to minimize the likelihood of damage or discomfort to the user's ear.

At the end of side straps 618 and 620 are mask connectors 628 that correspond to strap connectors 630 on mask 600. In this embodiment, mask connectors 628 and strap connectors 630 are shown as hook and loop tape. One skilled in the art will recognize that the type of adjustable attachment may vary and remain within the scope and spirit of the disclosure. The position of harness 602 in relation to mask 600 may be adjusted to further alter the comfort and seal of mask 600 on the user's face. In some embodiments, any excess length of side straps 618 and 620 may be cut off once a preferred engagement of mask 600 is determined for the user.

In addition, overhead straps 624 and 626 may be located near the meeting point of side straps 618 and 620 and during operation overhead straps 624 and 626 extend across the top of a user's head. In some embodiments, the connection of overhead straps 624 and 626 to side straps 618 and 620 may allow adjustments to customize the position of overhead straps 624 and 626 for the user. For example, in the depicted embodiment, the loops at the end of overhead straps 624 and 626 may slide forward and backward along side straps 618 and 620. In other embodiments, overhead straps 624 and 626 may be fixed to a specific location on side straps 618 and 620.

In this embodiment, during operation overhead straps 624 and 626 are connected near the top of a user's head. The connection of overhead straps 624 and 626 may be adjusted to provide lift on side straps 618 and 620 without creating excessive pressure across the top of a user's head which may cause skin damage or headaches. Hook and loop tape may be used to create the adjustable connection of overhead straps 624 and 626 over the top of a user's head. One skilled in the art will recognize that the type of adjustable connection may vary and remain within the scope and spirit of the disclosure. In some embodiments, overhead straps 624 and 626 is designed to lift side straps 618 and 620 above a user's ear in order to prevent potential discomfort or damage to the user's ear and skin.

FIG. 11 shows an embodiment of a mask 700 and harness 702 of an oxygen delivery system of the disclosure. Similar to other embodiments described herein, mask 700 is designed to fit a user's face, covering the nose and mouth of a user, and allows a user to breathe normally while providing conditioned air content. Mask 700 may be designed and operated as described further with regard to other embodiments disclosed herein. In this embodiment, mask 700 includes safety valve 704, access port 706, and contact rings 710. One skilled in the art will recognize that additional elements described elsewhere herein may be included in mask 700.

Safety valve 704 may be designed and utilized as described above. Safety valve 704 may operate to remove exhaled gas from mask 700 and/or improve the efficiency of the delivery of conditioned air content to a user. In this embodiment, an exhale valve is not included, and safety valve 704 is additionally operable to conduct the functions of the exhale valve as described elsewhere herein.

Mask 700 also includes access port 706 which is designed to operatively engage access port seals 708. Access port 706 allows access to provide a user with liquids, medicines, alternative airflow, and other items. Access port seals 708 provide a seal that allows straws, syringes, medicine droppers, thermometers, patient monitoring devices, and other supplies to pass through while minimizing loss of conditioned air from mask 700, and/or allow the connection of mask 700 to other medical systems. In this embodiment, the access port seals 708 shown include replaceable seals with (1) slits in a crossed or other shaped pattern to allow insertion of supplies, or (2) a tube connector. The design, characteristics, and operation of access ports and access port seals are described further elsewhere herein.

Contact rings 710 depicted in FIG. 11 represent elements that may be attached to or part of the edge of mask 700 that engages a user's face during operation. Contact rings 710 may include one or more of a molding element, a skin sensor element, and a skin protection element. These elements are described in more detail with respect to other embodiments herein, including the molding ring, skin sensor ring, and contact ring described with respect to FIG. 4. One skilled in the art will recognize that three rings are depicted for illustrative purposes and the functions and layering of the rings may vary and remain within the scope and spirit of the disclosure.

The inside of mask 700 may include one or more sanitary sheet 712 formed to match the internal walls of mask 700 without interfering with the operation of safety valve 704, access port 706, access port seals 708, or contact rings 710. Sanitary sheet 712 may be in removable contact with the internal walls of mask 700 or additional sanitary sheets 712. During use, sanitary sheet 712 may be periodically removed from the inside of mask 700 to expose a clean surface for ongoing operation of mask 700, increasing sanitary conditions for use of mask 700. Utilizing a removable sanitary sheet 712 may minimize the time that a user is without O2 delivery when the mask is removed for cleaning purposes.

In this embodiment, input port 716 is attached to the bottom of mask 700. As described above, input port 716 may be designed to allow slower velocity airflow into mask 700, and may help dampen the sound of airflow in the O2 delivery system.

In some embodiments, the oxygen delivery system may include a patient monitoring system that measures and records system operational characteristics, such as air pressure and air content in the system, and a user's physical characteristics, such as breathing rate, breath volume, and heart rate. For example, the system may include an airflow sensor that detects air pressure, air content, air flow rates, and volumetric changes in the air. The user, caregiver, or physician may review such characteristics to evaluate a user's health and/or ongoing treatment.

FIG. 12 shows an embodiment of a cannula 800 which may be used with an air delivery system, including but not limited to an air delivery system as described herein. Cannula 800 includes nostril inserts 802 configured for placement in operative association with a user's nostrils such that a seal or semi-sealed connection between the user's nostrils and the cannula is created. The nostril inserts 802 are tubes which may be made of a soft, flexible material that may conform to fit the contours of a user's nostrils providing a tight fit while limiting discomfort. The nostril inserts 802 may be designed with an opening approximating the size of a user's nostril while being structurally sufficient to maintain placement in a user's nostril and withstand air pressures in the cannula 800. The large tube size for the nostril inserts 802 allow a reduced velocity airflow while maximizing airflow into a user's pulmonary system. The sealed or semi-sealed connection further provides an efficient means of providing airflow to a user while minimizing the loss of oxygenated air to the ambient.

Nostril inserts 802 are operatively attached to compartment 804. In some embodiments, nostril inserts 802 may be formed as part of compartment 804, or as a separate attachable component. In some embodiments wherein nostril inserts 802 comprise an attachable component, nostril inserts 802 may be removably attached to compartment 804. For example, nostril inserts 802 may comprise a sleeve which slides on one or more extensions from compartment 804 to form a sealed friction attachment with compartment 804. In such a case, nostril inserts 802 may comprise a set of interchangeable sleeves, wherein nostril inserts 802 that best conform to a given user's nostrils may be selected from the set of interchangeable sleeves. Removable nostril inserts 802 may further be replaced periodically to improve sanitation. One skilled in the art will recognize that the forms of attachment may vary and remain within the scope and spirit of the disclosure.

In this embodiment, compartment 804 is designed to be larger than the cannula input tubing 808 which provides a velocity reduction prior to flowing into the user's nostrils. This velocity reduction relieves some discomfort that may be caused by higher velocity airflow into the nostrils. In this embodiment, smaller diameter tubing may be used for providing air to the velocity reduction compartment 804 at a high velocity, without directing the same velocity air to the user. One skilled in the art will recognize that air velocity may be reduced in a variety of manner, such as using larger diameter tubing throughout the system, and remain within the scope and spirit of the disclosure. However, some forms of reducing velocity may not be preferred because of their potential to irritate and/or cause discomfort to the user. For example, using large tubing throughout may increase the weight on the user's face, partially obstruct a user's view, and require additional components, such as adhesive tape, to hold the tubing in place.

Compartment 804 is rigid or semi-rigid such that alteration in airflow will not cause compartment 804 to collapse. Sufficient rigidity may be imparted through the selection of design materials and/or design features which provide structural rigidity. In some embodiment, at least a portion of compartment 804 in contact with the user's face will be made of a soft material to minimize discomfort and/or irritation caused by rubbing. In some embodiments, the portion of compartment 804 in contact with the user's face may be flat, semi-flat and/or contoured to fit the user's face. In some embodiments of cannula 800, nostril inserts 802 extend in a linear fashion from compartment 804. In other embodiments, nostril inserts 802 extend in a curved fashion from compartment 804.

In this embodiment, cannula tubing is formed to fit over a user's ears with earpiece 806. In some embodiments, cannula tubing is pre-formed into a rigid or semi-rigid earpiece 806. In other embodiments, cannula tubing is made of a moldable material whereby a user or healthcare provider may mold the tubing to fit a user's face and create a custom earpiece 806. One skilled in the art will recognize that the moldable quality may be developed into the cannula tubing and/or provided by an attachment to the cannula tubing. In some embodiments of cannula 800, other components include moldable features to customize the cannula 800 to a specific user.

In this embodiment, both ends of cannula tubing with earpiece 806 connect to cannula input tubing 808. Accordingly, in this embodiment, airflow from cannula input tubing 808 is directed into both ends of cannula tubing and flows into velocity reduction compartment 804 and to the user through nostril inserts 802. One skilled in the art will recognize that a cannula may be designed with tubing from one side of the user instead of the depicted versions with cannula tubing on both sides of a user's head, and remain within the scope and spirit of the present disclosure. In some embodiments, cannula tubing connects to cannula input tubing 808 by a fitted connection, a threaded connection, or another connection. In some embodiments, cannula input tube 808 and the cannula tubing is formed as a single tube.

Cannula in put tubing 808 extends to air delivery system connector 810. Air delivery system connector 810 is shown as a cap to connect to the output of an air delivery system. One skilled in the art will recognize that the air delivery system connector 810 may comprise any apparatus or system to attach cannula input tubing 808 to the selected air delivery system. Cannula 800 may be connected to a variety of air delivery systems, such as those described herein, oxygen tanks, and other air delivery systems.

FIG. 13 shows an embodiment of a cannula 900 which may be used with an air delivery system, including but not limited to an air delivery system as described herein. Similar to other embodiments described herein, cannula 900 includes nostril inserts 902 configured for placement in operative association with a user's nostrils. Nostril inserts 902 may be designed with a soft, flexible material which conforms to the contours of a user's nostrils, and with a large opening to allow reduced velocity airflow while maximizing airflow into a user's pulmonary system.

Nostril inserts 902 are in communicative association with compartment 904. As discussed above, nostril inserts 902 may be manufactured as part of compartment 904, or as a separate attachable component. Nostril inserts 902 may comprise a set of interchangeable sleeves, wherein nostril inserts 902 that best conform to a given user's nostrils may be selected from the set of interchangeable sleeves. Compartment 904 is designed larger than the cannula input tubing 908 and provides a velocity reduction prior to flowing into the user's nostrils. In some embodiment, compartment 904 includes a collapse resistant design and a flat, semi-flat and/or contoured contact portion to fit the user's face.

In this embodiment, cannula tubing is connected to head strap 906. Head strap 906 partially holds cannula 900 in place on the user's head, and guides cannula tubing over a user's ears to limit irritation or discomfort from rubbing against the user's ears. As described above, embodiments of cannula tubing may also be moldable. For example, cannula tubing may be molded around a user's ears to prevent and/or minimize contact with the user's ears. In some embodiments, head strap 906 is removably associated with cannula tubing. When engaged, head strap 906 limits the movement of cannula tubing around the head, but allows flexibility in cannula tubing behind the head. For example, cannula tubing may be loose or bowed between head strap 906 and tubing connector 912. The flexibility in cannula tubing behind the head allows a greater range of head movements by a user without irritation or unnecessary tugging at the tubing. Head strap 906 may also be adjustable to fit a range of head sizes comfortably.

In this embodiment, both ends of cannula tubing pass through head strap 906 and connect to cannula input tubing 908 through tubing connector 912. Cannula tubing and cannula input tubing 908 connect to tubing connector 912 by a fitted connection, a threaded connection, or another connection. In some embodiments, cannula tubing and cannula input tubing 908 may connect to tube connector 912 by different connection mechanisms. For example, in this embodiment, cannula tubing connects to tubing connector 912 by a fitted connection within tubing connector 912, while cannula input tubing 908 connects to the tubing connector 912 by external fitted connection 910.

Cannula in put tubing 908 extends to air delivery system connector 914. Air delivery system connector 914 is shown as a cap to connect to the output of an air delivery system. One skilled in the art will recognize that the air delivery system connector 914 may comprise any apparatus or system to attach cannula input tubing 908 to the selected air delivery system. Cannula 900 may be connected to a variety of air delivery systems, such as those described herein, oxygen tanks, and other air delivery systems.

FIG. 14 depicts an embodiment of a system with cannula 900 in operative association with components for an air delivery system as described elsewhere herein. In this embodiment, air delivery system connector 914 attaches to the output of air modification module 432. One skilled in the art will recognize that air modification module 432 and parts thereof may be designed and operated as described elsewhere herein. Air modification module 432 may mix the conditioned air supply with additives such as water vapor or medicine for the user to breathe.

Attached to air modification module 432 is input port tubing 218 which provides conditioned air to the user. In this embodiment, at the opposite end of input port tubing 218 is output coupling 220. Output coupling 220 connects the air modification module 432 to the flow rate throttling valve 222 through input port tubing 218, and also connects the air reservoir 226 via reservoir tube 224. Output coupling 220 includes a flow director that forces air to flow into the air reservoir 226. In this embodiment, flow rate throttling valve 222 is connected to output coupling 220 and air input port 430. One skilled in the art will recognize that the components shown in FIG. 14 may be designed and operated as described elsewhere herein.

The invention being thus described, it will be obvious that the same may be varied in many ways. Such variations are not to be regarded as a departure from the spirit and scope of the invention and all such modifications as would be obvious to one skilled in the art are intended to be included within the scope of the system, method, or apparatus described.

What is claimed:

1. An air delivery system comprising:
    a cannula comprising a velocity reduction compartment and nostril inserts, wherein said velocity reduction compartment is a structural chamber separate from said nostril inserts and wherein during operation said cannula is configured to be operatively associated with a user's breathing;
    cannula tubing facilitating airflow into said velocity reduction compartment, wherein said cannula tubing is configured to fit around the side of said user's head and comprises an earpiece section configured to fit above said user's ear, wherein said earpiece section is at least semi-rigid, and wherein said airflow exits said velocity reduction compartment through said nostril inserts;
    a flow rate throttling valve operatively associated with said cannula, wherein said flow rate throttling valve facilitates the airflow to said cannula via said cannula tubing, and wherein said flow rate throttling valve allows a minimum flow rate and varies the flow rate to maintain a positive pressure;
    an air source operatively associated with said flow rate throttling valve; and
    wherein said velocity reduction compartment reduces the flow rate of said airflow from said cannula tubing, and said airflow exits said velocity reduction compartment and enters said nostril inserts at a reduced flow rate, wherein said nostril inserts are shaped to maintain at least a minimum cross-sectional area to allow said airflow to pass through and exit said nostril inserts at said reduced flow rate.

2. The system according to claim 1, wherein during operation, said cannula is configured to create at least a partial seal with a nose of said user.

3. The system according to claim 1, further comprising an air modification module, wherein said air modification module transmits particles into said air.

4. The system according to claim 3, wherein said particles comprise at least one of water, saline, and medication.

5. The system according to claim 1, further comprising an air reservoir operatively associated with said cannula, wherein said air reservoir holds a reserve amount of air and when said air reservoir is compressed, said air delivery system is configured to provide said reserve air to said user.

6. The system according to claim 1, wherein said cannula comprises a head strap connected to said cannula tubing, wherein during operation said head strap is configured to hold said cannula in contact with said user's face and guide said cannula tubing over said user's ear.

7. A method for air delivery with an air delivery system comprising the steps of:
    securing a cannula in operative association with a user's nose, wherein said cannula comprises a velocity reduction compartment designed to limit access to ambient air and nostril inserts, wherein said velocity reduction compartment is a structural chamber separate from said nostril inserts and wherein said nostril inserts are configured to fit into said user's nose during operation and said nostril inserts are configured to maintain a cross-sectional area from an entrance of said nostril inserts to an exit of said nostril inserts;
    operating said air delivery system, wherein operation of said air delivery system comprises:
    providing airflow into a flow rate throttling valve, wherein said flow rate throttling valve facilitates the flow of air to said cannula through cannula tubing that is configured to fit around the side of said user's head and comprises an earpiece section configured to fit above said user's ear, wherein said earpiece section is at least semi-rigid,
    providing airflow into an air modification module, wherein said air modification module modifies air content within said air delivery system,
    providing airflow into an air reservoir, and
    providing airflow from said flow rate throttling valve and said air modification module to said cannula, wherein said airflow enters said velocity reduction compartment which reduces the flow rate of said airflow, and said airflow exits said velocity reduction compartment, enters said nostril inserts and passes through said nostril inserts at a reduced flow rate; and
    facilitating airflow at the reduced flow rate for inhalation by said user.

8. The method according to claim 7, wherein said cannula comprises a moldable material capable of retaining a form in which the material is molded, and said method comprises the step of molding said cannula into a shape configured to fit said user.

* * * * *